(12) United States Patent
Ju et al.

(10) Patent No.: US 9,809,630 B2
(45) Date of Patent: Nov. 7, 2017

(54) ENZYME-BASED PROTEIN SEPARATION AND ENRICHMENT FROM SOY MEAL, WHEAT MEAL, AND OTHER PROTEIN-RICH MATERIALS DERIVED FROM PLANT SEEDS, FRUITS AND OTHER BIOMASS

(71) Applicants: Lu-Kwang Ju, Akron, OH (US);
Abdullah Loman, Akron, OH (US);
Anthony Coffman, Canton, OH (US);
Qian Li, Cuyahoga Falls, OH (US);
Srujana Koganti, Akron, OH (US)

(72) Inventors: Lu-Kwang Ju, Akron, OH (US);
Abdullah Loman, Akron, OH (US);
Anthony Coffman, Canton, OH (US);
Qian Li, Cuyahoga Falls, OH (US);
Srujana Koganti, Akron, OH (US)

(73) Assignee: THE UNIVERSITY OF AKRON, Akron, OH (US)

( * ) Notice: Subject to any disclaimer, the term of this patent is extended or adjusted under 35 U.S.C. 154(b) by 0 days.

(21) Appl. No.: 14/400,076

(22) PCT Filed: May 9, 2013

(86) PCT No.: PCT/US2013/040332
§ 371 (c)(1),
(2) Date: Nov. 10, 2014

(87) PCT Pub. No.: WO2013/170017
PCT Pub. Date: Nov. 14, 2013

(65) Prior Publication Data
US 2015/0118730 A1  Apr. 30, 2015

Related U.S. Application Data
(60) Provisional application No. 61/644,565, filed on May 9, 2012.

(51) Int. Cl.
| | | |
|---|---|---|
| C12N 9/14 | (2006.01) |
| C07K 14/415 | (2006.01) |
| A23J 1/14 | (2006.01) |
| C12P 19/02 | (2006.01) |
| C12P 19/14 | (2006.01) |
| C12P 21/00 | (2006.01) |
| C12N 9/42 | (2006.01) |
| A23J 3/34 | (2006.01) |
| C12N 9/24 | (2006.01) |
| C12N 9/96 | (2006.01) |

(52) U.S. Cl.
CPC ............ *C07K 14/415* (2013.01); *A23J 1/148* (2013.01); *A23J 3/346* (2013.01); *C12N 9/248* (2013.01); *C12N 9/2437* (2013.01); *C12N 9/96* (2013.01); *C12P 19/02* (2013.01); *C12P 19/14* (2013.01); *C12P 21/00* (2013.01); *C12Y 302/01004* (2013.01); *C12Y 302/01008* (2013.01); *C12Y 302/01015* (2013.01)

(58) Field of Classification Search
None
See application file for complete search history.

(56) References Cited

U.S. PATENT DOCUMENTS

| 3,042,584 | A | 7/1962 | Kooi et al. |
| 4,863,613 | A | 9/1989 | Johnson et al. |
| 4,897,465 | A | 1/1990 | Cordle et al. |
| 6,313,273 | B1 | 11/2001 | Thomas et al. |
| 6,818,246 | B2 | 11/2004 | Singh |
| 8,658,407 | B2 * | 2/2014 | Lyons ................ A23K 1/007 435/161 |
| 8,679,794 | B2 * | 3/2014 | Muniglia ............ A23D 9/02 435/209 |
| 2007/0077630 | A1 | 4/2007 | Harris et al. |

(Continued)

FOREIGN PATENT DOCUMENTS

| WO | WO 2011045387 | * | 4/2011 |
| WO | 2012021410 A1 | | 2/2012 |

OTHER PUBLICATIONS

Brijwani et al., Process Biochemistry 45 (2010) 120-128.*
Stanojevic et al., Bulgarian Journal of Agricultural Science, 15 (No. 4) 2009, 307-311.*
NRRL (1) and (2) (http://nrrl.ncaur.usda.gov/cgi-bin/usda/process.html), accessed May 5, 2016.*
Mandels et al. In Hajny and Reese; Cellulases and Their Applications, Advances in Chemistry; American Chemical Society: Washington, DC, 1969, pp. 391-413.*

(Continued)

*Primary Examiner* — Irene Marx
(74) *Attorney, Agent, or Firm* — Renner Kenner Greive Bobak Taylor & Weber

(57) ABSTRACT

The present invention is directed to enzyme based methods for separating protein from protein-rich materials derived from plant seeds, fruit, or other biomass and products made therefrom. The protein content in the resulting products is improved by separating and removing the carbohydrates from around the proteins in, for example, soybean meal. This removal is facilitated by the enzymatic hydrolysis of poly- and oligomeric carbohydrates into monosaccharides and other water soluble sugars. The present invention provides for the production of three streams of useful materials. The first is an enriched protein material comparable to the known SPCs but without significant quantities of undigestible oligosaccharides and polysaccharides. The second is an SPI made from the soluble protein in the hydrolysate which is valuable for high-quality feed, food and industrial uses. The third is the soluble saccharides and hydrolyzed carbohydrates (releasing sugars) that can be converted by fermentation to various valuable bioproducts.

23 Claims, 12 Drawing Sheets

(56) References Cited

U.S. PATENT DOCUMENTS

2007/0172914 A1* 7/2007 Slabbekoorn ........... A23J 1/005
                                                     435/68.1
2009/0280105 A1  11/2009 Gusakov et al.
2012/0196332 A1   8/2012 Muniglia et al.

OTHER PUBLICATIONS

Jahangeer, S. et al., "Screening and Characterization of Fungal Cellulases Isolated from the Native Environmental Source," Pak. J. Bot., 37(3):739-748 (2005).

Zheng, Y. et al., "Enzymatic saccarification of dilute and pretreated saline crops for fermentable sugar production," Applied Energy 86 (2009) 1459-2465.

Wang, C.L. et al., "Effects of Alpha-galactosidase Supplementation to Corn-soybean Meal Diets on Nutrient Utilization, performance, Serum Indices and Organ Weight in Broilers," Asian-Aust. J. Anim. Sci. 2005. vol. 18, No. 12: 1761-1768.

\* cited by examiner

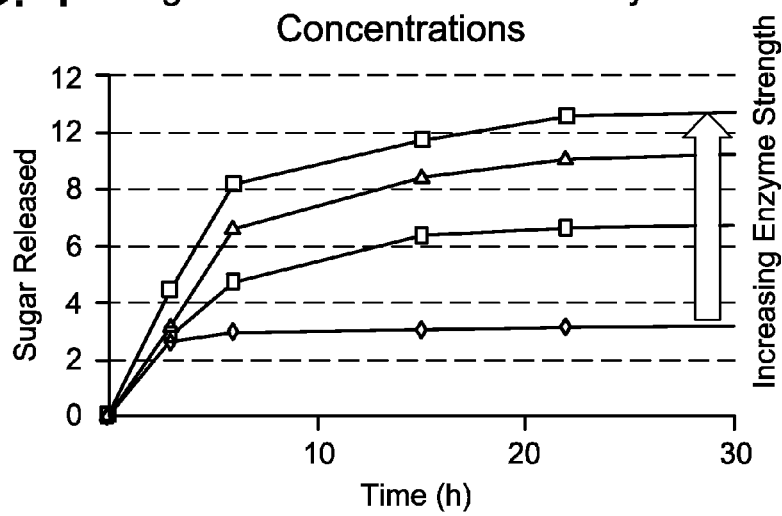
FIG. 1 Sugar Release at Different Enzyme Concentrations
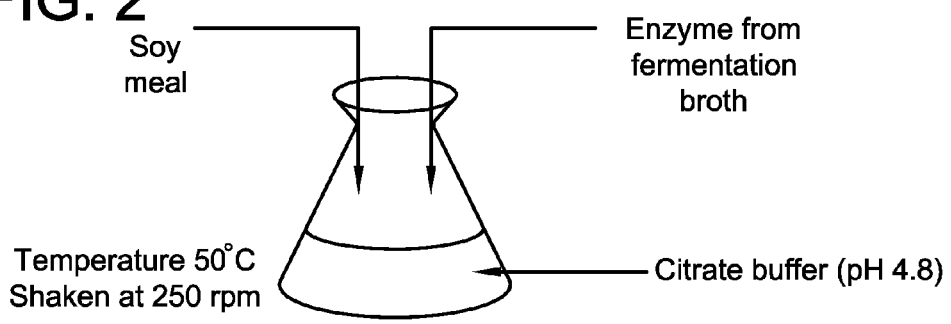
FIG. 2
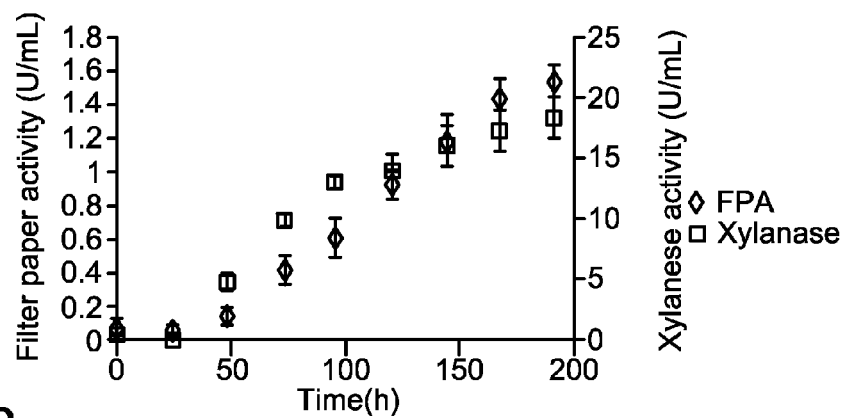
FIG. 3

ENZYME-BASED PROTEIN SEPARATION AND ENRICHMENT FROM SOY MEAL, WHEAT MEAL, AND OTHER PROTEIN-RICH MATERIALS DERIVED FROM PLANT SEEDS, FRUITS AND OTHER BIOMASS

CROSS REFERENCE TO RELATED APPLICATIONS

This application claims the benefit of U.S. provisional patent application Ser. No. 61/644,565 entitled "Enzyme-Based Protein Separation and Enrichment From Soy Meal, Wheat Meal, and Other Protein-Rich Materials Derived From Plant Seeds," filed May 9, 2012, and incorporated by reference in its entirety.

FIELD OF THE INVENTION

The present invention is directed to an enzyme based method of separating protein from protein-rich material derived from plant seeds, fruits and other biomass. The present invention uses the enzymes (e.g., from *Trichoderma reesei* and/or *Aspergillus niger* fermentation) which are preferably mixtures of at least cellulase, xylanase and pectinase to effectively hydrolyze almost all of the polymeric and oligomeric carbohydrates present in protein-rich materials derived from plant seeds such as soybean meal, leading to production of soy protein products with high protein contents and suitable to be included in the animal feed and human food products as well as a monosaccharide-rich liquid for use in fermentation.

BACKGROUND OF THE INVENTION

Soybean is probably the best protein source among possible plant feed stuffs available having reasonable amino acid profiles that could be used as an alternative to animal protein. Soy protein products are used in various kinds of foods such as infant formulas, soups, meat analogues, tofu, frozen foods, etc. Soy protein products are also used to improve texture of meat products, increase the protein content of the food, to enhance moisture retention and also as an emulsifier. The major factors that drive the soy protein market are functionality, health benefits, environment friendliness, cost and versatility. Among all plant proteins, soy protein is the most similar to the animal protein in terms of amino acids and soy protein is much cheaper than animal protein. Worldwide soy protein market in terms of revenue had a worth of $5 billion in 2011 and is expected to reach $9 billion by 2017. Asian market is expected to be the fastest growing market in upcoming future due to its advancement and increasing demand from China and India. North America especially United States dominates the global soy protein market right now, accounting for more than 35% of the global soy protein market demand in 2012.

Successful inclusion of soy proteins into various animal feed or human food products such as aquaculture feed for fish and shrimp, poultry feed, and meat, typically requires the proteins to exhibit similar characteristics to those of the proteins being replaced or supplemented in the feed or food. Different functional properties of soy proteins are required in varying degrees to be included in different kinds of food. And the functionality is affected by the methods used to make the soy protein products.

Many plant seeds, like soy beans, wheat, pulse, peas, or chickpeas, contain a significant amount of usable protein, together with some fats and both soluble and insoluble carbohydrates. Soybean meal, for example, contains approximately 30-35% carbohydrates, mostly non-starch polysaccharides (NSPs) and oligosaccharides. The soluble carbohydrates and the fats can easily be removed by conventional methods, leaving the protein material and the insoluble oligosaccharides and polysaccharides. These oligo- and, particularly, poly-saccharides have been found to lower digestibility of soy products when included in animal feed.

Processed defatted soybean products are typically divided into three categories: soy flour, Soy Protein Concentrate (SPC) and Soy Protein Isolate (SPI). As used herein, soy flour is a powdery defatted soybean meal containing about 50% protein. As used herein, SPC is any soybean meal products processed to have protein contents higher than that of soy flour but lower than that of SPI. The typical SPC has protein content in the range of 65% to 75%. As used herein, SPI refers to any soybean meal products processed to have a protein content of at least 90%. As used herein, the term "soybean hulls" refers to the soybean seed coats, which are removed and collected while soybeans are processed for soybean oil and soybean meal products. As used herein, "soybean flakes" refers to the soybean meal products processed into a physical shape of flakes. As used herein, "soybean powder" refers to the soybean meal products processed into a physical shape of powders.

Current commercial processes for producing SPC and SPI use non-enzymatic methods. SPC is currently produced by washing soy flour with water, often containing a pH buffer and/or an organic solvent. The water soluble carbohydrates (and other soluble and colloidal materials) are removed from the mixture to leave the protein-rich solids that remain. SPC thus produced usually has a protein content of about 65-70% but retains the insoluble soy carbohydrates including the non-starch polysaccharides (hemi/cellulose and pectin), and lignin. The protein yield (i.e., the portion of initial proteins retained in the product) for SPC production can be high (90%-98% depending on the method), but it is less ideal for many uses because of the presence of the hard to digest polymers.

SPI, on the other hand, is currently prepared by first dissolving proteins in aqueous solutions, together with water soluble carbohydrates and others. This causes disintegration of soybean meal particles and allows removal of insoluble constituents by centrifugation. Proteins in the supernatant are then made insoluble, for example by adjusting the pH with acid to a particular pH where the proteins precipitate out and collected by centrifugation. The SPI product thus prepared has higher protein content (about 90%) but is costly to produce and gives a dry weight yield of only about only 30% (protein yield about 60%).

Moreover, many SPC or SPI products are also currently made using methods that include alcohol leaching or treating with acid. Soy proteins obtained using alcohol leaching have been found to have a much lower nitrogen solubility index (NSI), which results in a lower functionality of the product. This is because the protein has been denatured to a greater extent by the alcohol and the heat used in the alcohol leaching process. Further, during the conventional acid wash or alcohol leaching process, some of the alcohol and/or acid remains in the soy protein precipitates and must be removed by additional processing. This additional processing makes the process less economical or may be sufficiently harsh to reduce the value and protein content of the product.

The high content of non-starch polysaccharides (NSPs) in soybean meal and SPC produced by the current processes as described above is a major challenge to the use of soy products, particularly as animal feeds. It is believed that soybean NSPs in feed may have the effect of increasing the viscosity of the intestinal content, which might also be a reason for poor digestibility of nutrients in these animal feeds. Soybean meal contains almost 15% oligosaccharides and 20% NSPs. Soy protein concentrate (SPC) produced by the current commercial method contains 3-5% oligosaccharides and 14-17% NSPs, which have been reported to be indigestible to fish. Reduced digestibility of fat and proteins in Atlantic salmon, for example, have been reported due to the presence of dietary NSPs in soybean meal. (See Storebakken, T., S. Refstie, and B. Ruyter, *Soy products as fat and protein sources in fish feeds for intensive aquaculture*. Soy in Animal Nutrition, 2000: p. 127-170, the disclosure of which is incorporated herein by reference in its entirety). These components were reported to be responsible for low growth performance and induced enteritis in several salmonids species fed with soybean meal-containing diet.

Another problem with the conventional production processes is the presence of non-functional indigestible fibers in the final product. Natural soy fiber is derived from the parenchyma cell walls of the soybean. The presence of these fibers can bind with the otherwise digestible proteins to prevent the soy products from being used in various animal feed.

In addition, the prior art processes remove the soluble material from the soybean meal either by washing it with large quantities of water or by treating with acid or leaching with alcohol and as a result, it is often not practical to try to utilize the soluble material for other purposes. The prior art processes do not do anything to break down the soluble oligosaccharides, such as raffinose, stachyose and verbascose, into easily fermentable sugars. These oligosaccharides are not readily metabolizable to many organisms and are a hindrance in many industrial applications. In addition, because neither the soluble and insoluble oligosaccharides nor the polysaccharides are broken down into fermentable sugars and a very large quantity of water may be used to wash the soybean meal, the concentration of fermentable sugars in the wash water is not high enough to justify further processing. Moreover, the large quantity of wash water used likewise makes it difficult to easily recover the soluble proteins. And, as discussed above, where the soy proteins obtained using alcohol leaching have been found to have a much lower nitrogen solubility index (NSI) and where the conventional acid wash or alcohol leaching processes are used, some of the alcohol and/or acid remains in the soy protein precipitates and must be removed by additional processing.

Therefore, there is a need in the art for more economic processes for producing soy products having a high protein content and low level of indigestible components, while at the same time generating and capturing the monosaccharide-rich liquid byproduct of the process for future use.

SUMMARY OF THE INVENTION

The present invention is directed an enzyme based method for separating protein from protein-rich, or at least protein-containing, materials derived from plant seeds, fruit, or other biomass and products made therefrom. The protein content in the resulting products is improved by separating and removing the carbohydrates (and other minor components) from in and around the proteins in, for example, soybean meal. This removal is facilitated by the enzymatic hydrolysis of poly- and oligomeric carbohydrates and other non-protein materials into monosaccharides and other water soluble sugars. Further, a significant amount of soluble protein and other materials are trapped within and around these oligosaccharides and polysaccharides. As these carbohydrates are broken down by enzyme hydrolysis into increasingly smaller sugars, it becomes easier for the larger trapped proteins to separate from the smaller saccharides.

The present invention provides for the production of three streams of useful materials. The first is an enriched protein material comparable to the SPCs of the prior art, containing the non-water-soluble proteins fats, and other materials not hydrolyzed by the enzymes. Unlike the SPCs of the prior art, however, this enriched protein material does not have the significant quantities of undigestible oligosaccharides and polysaccharides. This material may be dried to a protein powder or used in another form (e.g. a protein paste, protein mixture or protein solution). The second is an SPI made from the soluble protein in the hydrolysate. These enriched proteins (the enriched protein material and the SPI) are valuable for high-quality feed, food and industrial uses. The third stream is the soluble saccharides and hydrolyzed carbohydrates (releasing sugars) that can be converted by fermentation to various valuable bioproducts.

In one aspect, the present invention is directed to an enzyme based method of separating protein from protein-containing material derived from plant seeds, fruits or other biomass comprising the steps of: (a) combining a protein-containing material derived from plant seeds, fruits or other biomass with a liquid enzyme medium comprising at least one cellulase, at least one hemicellulase, and at least one pectinase; (b) mixing the mixture of step A, wherein the at least one cellulase enzyme, at least one hemicellulase enzyme, and at least one pectinase enzyme in the liquid enzyme medium will hydrolyze the polysaccharides and oligosaccharides contained in the protein-containing material into saccharides that are soluble in the liquid enzyme medium to leave a solid protein material in the liquid enzyme medium; and (c) collecting the protein from the liquid enzyme medium. In some other embodiments, the method of separating protein from protein-containing material may include any of the embodiments described above and further comprises the step of drying the collected protein material to form a protein-containing powder.

In some other embodiments, the method of separating protein from protein-containing material may include any of the embodiments described above and further comprises the steps of adding additional batches of the protein-containing material as the previous batches of the protein-containing material are hydrolyzed.

In some embodiments, the method of separating protein from protein-containing material may include any of the embodiments described above wherein the protein-containing material is derived from soy beans. In some embodiments, the method of separating protein from protein-containing material may include any of the embodiments described above wherein the protein-containing material is soybean meal, soy flour, soy flake, or soy powder.

In some embodiments, the method of separating protein from protein-containing material may include any of the embodiments described above and further comprises the step of heating the protein-containing material to a temperature of from about 155° C. to about 200° C. for a period of from about 30 minutes to 5 hours to reduce the growth of bacterial and other contaminants during hydrolysis.

In some embodiments, the method of separating protein from protein-containing material may include any of the embodiments described above wherein the pH of the liquid enzyme medium in step (a) is about 4.6 to about 5.2. In some embodiments, the method of separating protein from protein-containing material may include any of the embodiments described above wherein the pH of the liquid enzyme medium in step (a) is from about 4.8 to about 5.0. In some embodiments, the method of separating protein from protein-containing material may include any of the embodiments described above wherein the pH of the liquid enzyme medium in step (a) is about 4.8.

In some embodiments, the method of separating protein from protein-containing material may include any of the embodiments described above wherein the temperature of the liquid enzyme medium in step A is from about 20° C. to about 35° C. In some embodiments, the method of separating protein from protein-containing material may include any of the embodiments described above wherein the temperature of the liquid enzyme medium in step A is from about 28° C. to about 30° C.

In some embodiments, the method of separating protein from protein-containing material may include any of the embodiments described above wherein the mixture of step (b) is kept at a pH of from about 4.8 to about 5.0. In some embodiments, the method of separating protein from protein-containing material may include any of the embodiments described above wherein the mixture of step (b) is kept at a pH of about 4.8.

In some embodiments, the method of separating protein from protein-containing material may include any of the embodiments described above wherein the temperature of step (b) is about 45° C. to about 50° C. In some embodiments, the method of separating protein from protein-containing material may include any of the embodiments described above wherein the temperature of step (b) is about 50° C.

In some embodiments, the method of separating protein from protein-containing material may include any of the embodiments described above wherein the mixture of step (b) is mixed for a period of from about 1 hour to about 96 hours. In some embodiments, the method of separating protein from protein-containing material may include any of the embodiments described above wherein the mixture of step (b) is mixed for a period of from about 4 hours to about 48 hours. In some embodiments, the method of separating protein from protein-containing material may include any of the embodiments described above wherein the mixture of step (b) is mixed for a period of from about 8 hours to about 24 hours.

In some embodiments, the method of separating protein from protein-containing material may include any of the embodiments described above wherein the solid protein material is separated from the liquid enzyme medium using a centrifuge. In some embodiments, the method of separating protein from protein-containing material may include any of the embodiments described above wherein the solid protein material is separated from the liquid enzyme medium using filtration.

In some embodiments, the method of separating protein from protein-containing material may include any of the embodiments described above wherein the liquid enzyme medium is made from the fermentation of one or more fungus selected from the genera consisting of *Trichoderma, Aspergillus, Penicillium, Saccharomyces, Phanerochaete, Rhizopus, Fusarium, Neurospora, Podospora, Pichia*, and *Schizophyllum*.

In some embodiments, the method of separating protein from protein-containing material may include any of the embodiments described above wherein the one or more fungus further comprises a fungus selected from the group consisting of *Trichoderma reesei* Rut-C30 NRRL 11460, *Aspergillus niger* NRRL 322, *Aspergillus niger* NRRL 325, *Aspergillus niger* NRRL 328, *Aspergillus niger* NRRL 334, *Aspergillus niger* NRRL 341, *Aspergillus niger* NRRL 348, *Aspergillus niger* NRRL 363, *Aspergillus niger* NRRL 566, *Aspergillus niger* NRRL 599, *Aspergillus niger* NRRL 2270, *Aspergillus niger* NRRL 13201, *Aspergillus niger* NRRL 13219, *Aspergillus niger* NRRL 62517 and *Aspergillus aculeatus* NRRL 2053.

In some embodiments, the method of separating protein from protein-containing material may include any of the embodiments described above wherein the liquid enzyme medium is made from the fermentation of *Trichoderma reesei*. In some other embodiments, the method of separating protein from protein-containing material may include any of the embodiments described above wherein the liquid enzyme medium is made from the fermentation of *Aspergillus niger*. In some embodiments, the method of separating protein from protein-containing material may include any of the embodiments described above wherein the liquid enzyme medium is made from the fermentation of *Aspergillus niger* NRRL 322. In some embodiments, the method of separating protein from protein-containing material may include any of the embodiments described above wherein the liquid enzyme medium is made from the fermentation of *Aspergillus niger* NRRL 341.

In some embodiments, the method of separating protein from protein-containing material may include any of the embodiments described above wherein the mixture of Step (a) further comprises an antimicrobial agent selected from the group consisting of sodium benzoate, benzoic acid, sodium azide, ethylenediaminetetraacetic acid (EDTA) and sodium nitrite.

In some embodiments, the method of separating protein from protein-containing material may include any of the embodiments described above wherein the liquid enzyme medium is made by the steps of: (a) forming a seed culture by placing at least one fungus, a first carbon source, and a first nitrogen source in a container and agitating for from about 12 to about 96 hours at a temperature of from about 20° C. to about 35° C.; (b) transferring the contents of the seed culture to a fermentation vessel that contains a medium with at least a second carbon source, a second nitrogen source and water; (c) adjusting the pH of the contents of the fermentation vessel to a pH of from about 3 to about 8; (d) growing the fungus in the fermentation vessel; (e) collecting the product of step D, which comprises a mixture of a solid waste material and an enzyme-containing liquid; (f) separating the solid waste material from the enzyme-containing liquid and collecting the enzyme-containing liquid; and (g) diluting the enzyme-containing liquid of step F with water or an aqueous solution in a ratio of from about 1:1 to about 50:1 water or solution to enzyme-containing liquid. In some embodiments, the method of separating protein from protein-containing material may include any of the embodiments described above wherein the ratio of enzyme medium to protein-containing material is from about 3:1 to about 10:1 volume to weight.

In some embodiments, the method of separating protein from protein-containing material may include any of the embodiments described above wherein the hemicellulase is one or more enzyme selected from the group consisting of xylanase, mannanase, α-galactosidase, α-arabinosidase, β-xylosidase and acetyl xylan esterase. In some embodiments, the method of separating protein from protein-containing material may include any of the embodiments described above wherein the hemicellulase is a xylanase. In some embodiments, the method of separating protein from protein-containing material may include any of the embodiments described above wherein the pectinase is one or more enzyme selected from the group consisting of protopectinases, esterases, depolymerases, pectinesterase, polygalacturonase galacturan 1,4-α-galacturonidase, exo-poly-α-galacturonosidase, pectate lyase, pectate disaccharide-lyase, oligogalacturonide lyase and pectin lyase.

In another aspect, the present invention is directed to a method of producing enzymes for use in the hydrolysis of polysaccharides and oligosaccharides in soybean meal, soy flour, soy flake and soy powder comprising the steps of: (a) forming a seed culture by placing at least one fungus, a first carbon source, and a first nitrogen source in a container and agitating for about 72 hours at a temperature of from about 20° C. to about 35° C.; (b) transferring the contents of the seed culture to a fermentation vessel and adding a second carbon source, a second nitrogen source and water; (c) adjusting the pH of the contents of the fermentation vessel to a pH of from about 3 to about 5; (d) growing the fungus in the fermentation vessel; and (e) collecting the product of step (d), which comprises a mixture of a solid waste material and an enzyme-containing liquid.

In some embodiments, the method of producing enzymes for use in hydrolysis may include any of the embodiments described above and further comprises the steps of separating the solid waste material from the enzyme-containing liquid and collecting the enzyme-containing liquid.

In some embodiments, the method of producing enzymes for use in hydrolysis may include any of the embodiments described above and further comprises the step of creating a liquid enzyme medium for use in hydrolysis by diluting the enzyme-containing liquid with water in a ratio of from about 5:1 to about 20:1 water to enzyme-containing liquid. In some embodiments, the method of producing enzymes for use in hydrolysis may include any of the embodiments described above and further comprises the step of adjusting the pH of the diluted enzyme-containing liquid to a pH of from about 4.6 to about 5.2. In some embodiments, the method of producing enzymes for use in hydrolysis may include any of the embodiments described above and further comprises the step of adding an antimicrobial agent selected from the group consisting of sodium benzoate, benzoic acid, sodium azide, ethylenediaminetetraacetic acid (EDTA), and sodium nitrite to the liquid enzyme medium.

In some embodiments, the method of producing enzymes for use in hydrolysis may include any of the embodiments described above wherein the seed culture of step (a) further comprises an inducer, the inducer inducing the at least one fungus to produce enzymes. In some embodiments, the method of producing enzymes for use in hydrolysis may include any of the embodiments described above wherein the mixture of step B further comprises an inducer, the inducer inducing the at least one fungus to produce enzymes. In some embodiments, the method of producing enzymes for use in hydrolysis may include any of the embodiments described above wherein the inducer is the first carbon source or the first nitrogen source. In some embodiments, the method of producing enzymes for use in hydrolysis may include any of the embodiments described above wherein the inducer is the second carbon source or the second nitrogen source.

In some embodiments, the method of producing enzymes for use in hydrolysis may include any of the embodiments described above wherein the enzymes further comprise at least one cellulase, at least one hemicellulase, and at least one pectinase. In some embodiments, the method of producing enzymes for use in hydrolysis may include any of the embodiments described above and further comprises the steps of agitating the contents of the fermentation vessel and adding air, oxygen, or a combination thereof to the fermentation vessel until the enzyme production has substantially stopped. In some embodiments, the method of producing enzymes for use in hydrolysis may include any of the embodiments described above wherein the dissolved oxygen concentration of the material in the fermentation vessel of step B is maintained above about 5%. In some embodiments, the method of producing enzymes for use in hydrolysis may include any of the embodiments described above wherein the dissolved oxygen concentration of the material in the fermentation vessel is maintained above about 10%. In some embodiments, the method of producing enzymes for use in hydrolysis may include any of the embodiments described above wherein the dissolved oxygen concentration of the material in the fermentation vessel is maintained above about 20%.

In some embodiments, the method of producing enzymes for use in hydrolysis may include any of the embodiments described above wherein the enzyme-containing liquid is separated from the solid waste material using a centrifuge. In some embodiments, the method of producing enzymes for use in hydrolysis may include any of the embodiments described above wherein the enzyme-containing liquid is separated from the solid waste material by filtration.

In some embodiments, the method of producing enzymes for use in hydrolysis may include any of the embodiments described above wherein the first carbon source is selected from the group consisting of soy hulls, potato dextrose, sucrose, lactose, glucose, fructose, maltose, glycerol, the hydrolysate generated from the enzyme-hydrolysis process, other soluble soy carbohydrates, and other carbohydrates, proteins, lipids, fat, fatty acids, glycerides, and mixtures thereof.

In some embodiments, the method of producing enzymes for use in hydrolysis may include any of the embodiments described above wherein the first nitrogen source is selected from (1) organic nitrogen-containing materials such as proteins, nucleic acids, corn steep liquor, milk, dairy products and waste, peptides, amino acids, yeast extract, tryptone, peptone, other protein digests (including the proteins present in the hydrolysate generated from the enzyme hydrolysis process), and urea; (2) inorganic nitrogen-containing materials particularly ammonia, various ammonium salts (for example, ammonium sulfate, ammonium chloride, and ammonium phosphate) and various nitrates (for example, sodium nitrate, ammonium nitrate, potassium nitrate, calcium nitrate, magnesium nitrate, and nitric acid); and (3) mixtures of the above organic and inorganic nitrogen-containing materials. In some embodiments, the method of producing enzymes for use in hydrolysis may include any of the embodiments described above wherein the first nitrogen source is selected from the group consisting of soybean meal, soy flour, corn steep liquor, dairy waste containing milk protein, and a mixture of from about 0 g/L to about 2.65 g/L of Ammonium Sulfate, from about 0 g/L to about 0.3 g/L of urea, and from about 0 g/L to about 3.47 g/L of Proteose peptone.

In some embodiments, the method of producing enzymes for use in hydrolysis may include any of the embodiments described above wherein the second carbon source is selected from the group consisting of soy hulls, sucrose, lactose, and/or other soluble soy carbohydrates. In some embodiments, the method of producing enzymes for use in hydrolysis may include any of the embodiments described above wherein the second nitrogen source is selected from the group consisting of soy flour and a mixture of from about 0 g/L to about 2.65 g/L of Ammonium Sulfate, from about 0 g/L to about 0.3 g/L of urea, and from about 0 g/L to about 3.47 g/L of Proteose peptone.

In some embodiments, the method of producing enzymes for use in hydrolysis may include any of the embodiments described above wherein the at least one fungus comprises a *Trichoderma reesei*. In some embodiments, the method of producing enzymes for use in hydrolysis may include any of the embodiments described above wherein the at least one fungus comprises an *Aspergillus niger*.

In some embodiments, the method of producing enzymes for use in hydrolysis may include any of the embodiments described above wherein the at least one fungus comprises one or more fungus selected from the group consisting of *Trichoderma reesei* Rut-C30 NRRL 11460, *Aspergillus niger* NRRL 322, *Aspergillus niger* NRRL 325, *Aspergillus niger* NRRL 328, *Aspergillus niger* NRRL 334, *Aspergillus niger* NRRL 341, *Aspergillus niger* NRRL 348, *Aspergillus niger* NRRL 363, *Aspergillus niger* NRRL 566, *Aspergillus niger* NRRL 599, *Aspergillus niger* NRRL 2270, *Aspergillus niger* NRRL 13201, *Aspergillus niger* NRRL 13219, *Aspergillus niger* NRRL 62517 and *Aspergillus aculeatus* NRRL 2053. In some embodiments, the method of producing enzymes for use in hydrolysis may include any of the embodiments described above wherein the at least one fungus comprises an *Aspergillus niger* NRRL 322. In some embodiments, the method of producing enzymes for use in hydrolysis may include any of the embodiments described above wherein the at least one fungus comprises an *Aspergillus niger* NRRL 341.

In some embodiments, the method of producing enzymes for use in hydrolysis may include any of the embodiments described above wherein the temperature of step (a) is from about 15° C. to about 50° C. In some embodiments, the method of producing enzymes for use in hydrolysis may include any of the embodiments described above wherein the temperature of growing the fungus in the fermentation vessel and collecting the product is from about 15° C. to about 50° C.

In another aspect, the present invention is directed to a method of making monosaccharide-containing liquid for use in fermentation comprising the steps of: (a) combining a protein-containing material with a liquid enzyme medium comprising at least one cellulase, at least one hemicellulase, and at least one pectinase, the liquid enzyme medium; (b) stirring or agitating the mixture of step A wherein the at least one cellulase, at least one hemicellulase, and at least one pectinase enzymes in the liquid enzyme medium will hydrolyze the polysaccharides and oligosaccharides contained in the protein-containing material into monosaccharides and other sugars that are soluble in the liquid enzyme medium; (c) collecting the monosaccharide-containing liquid and heating it to a temperature of about 60° C. to about 100° C. to precipitate out dissolved proteins and other biopolymers that can be denatured by high temperature; and (d) collecting the monosaccharide-containing liquid. In some embodiments, the method of making a monosaccharide-containing liquid for use in fermentation may include any of the embodiments described above wherein the ratio of the volume of the liquid enzyme medium to the weight of the soy meal in step (a) is from about 3:1 to about 10:1.

In some embodiments, the method of making a monosaccharide-containing liquid for use in fermentation may include any of the embodiments described above wherein the dissolved proteins and other biopolymers in the monosaccharide-containing liquid are forced to precipitate out of solution by adjusting the pH of the monosaccharide-containing liquid to the isoelectric point of each one of the dissolved proteins and other biopolymers. In some embodiments, the method of making a monosaccharide-containing liquid for use in fermentation may include any of the embodiments described above wherein the pH of the liquid enzyme medium is adjusted to be from about 4.3 to about 4.7.

In some embodiments, the method of making a monosaccharide-containing liquid for use in fermentation may include any of the embodiments described above wherein the dissolved proteins and other biopolymers in the monosaccharide-containing liquid are forced to precipitate out of solution by diluting the monosaccharide-containing liquid with water or an aqueous solution. In some embodiments, the method of making a monosaccharide-containing liquid for use in fermentation may include any of the embodiments described above wherein the dissolved proteins and other biopolymers in the monosaccharide-containing liquid are forced to precipitate out of solution by the addition of ethanol.

In some embodiments, the method of making a monosaccharide-containing liquid for use in fermentation may include any of the embodiments described above wherein the enzyme medium is made according to the method steps of: (a) forming a seed culture by placing at least one fungus, a first carbon source, and a first nitrogen source in a container and agitating for about 72 hours at a temperature of from about 20° C. to about 35° C.; (b) transferring the contents of the seed culture to a fermentation vessel and adding a second carbon source, a second nitrogen source and water; (c) adjusting the pH of the contents of the fermentation vessel to a pH of from about 3 to about 5; (d) growing the fungus in the fermentation vessel; (e) collecting the product of step (d), which comprises a mixture of a solid waste material and an enzyme-containing liquid; (f) separating the solid waste material from the enzyme-containing liquid and collecting the enzyme-containing liquid; and (g) diluting the enzyme-containing liquid with water in a ratio of from about 5:1 to about 20:1 water to enzyme-containing liquid.

In some embodiments, the method of making a monosaccharide-containing liquid for use in fermentation may include any of the embodiments described above wherein the precipitated proteins of step (c) are removed from the monosaccharide-containing liquid using a centrifuge.

In some embodiments, the method of making a monosaccharide-containing liquid for use in fermentation may include any of the embodiments described above and further comprises the step of adding an antimicrobial agent selected from the group consisting of sodium benzoate, benzoic acid, sodium azide, ethylenediaminetetraacetic acid (EDTA), and sodium nitrite to the mixture of step (a). In some embodiments, the method of making a monosaccharide-containing liquid for use in fermentation may include any of the embodiments described above and further comprises the step of removing the microbial agent from the monosaccharide-containing liquid of step (d) by extraction using buterol, methanol, propanol, acetone, tetrahydrofuran or combinations thereof. In some embodiments, the method of making a monosaccharide-containing liquid for use in fermentation may include any of the embodiments described above and further comprises the step of removing the microbial agent from the monosaccharide-containing liquid of Step (d) by filtration through granulated activated carbon.

In some embodiments, the method of making a monosaccharide-containing liquid for use in fermentation may include any of the embodiments described above and further comprises the step of heating the protein-containing material to a temperature of from about 155° C. to about 200° C. for a period of from about 30 minutes to 5 hours to reduce the growth of bacterial and other contaminants during hydrolysis.

In another aspect, the present invention is directed to a method of making a soy protein isolate comprising the steps of: (a) combining protein containing material selected from the group consisting of soybean meal, soy flour, soy flake, soy powder or combinations thereof with a liquid enzyme medium comprising at least one cellulase, at least one hemicellulase, and at least one pectinase; (b) stirring or agitating the mixture of step (a), wherein the at least one cellulase, at least one hemicellulase, and at least one pectinase enzymes in the liquid enzyme medium will hydrolyze the polysaccharides and oligosaccharides contained in the protein-containing material into monosaccharides and other sugars that are soluble in the liquid enzyme medium and dissolving any water soluble proteins; (c) collecting the dissolved protein-containing liquid and heating it to a temperature of from about 60° C. to about 100° C. to precipitate out the dissolved proteins; and (d) collecting the precipitated proteins as a soy protein isolate.

In some embodiments, the method of making a soy protein isolate may include any of the embodiments described above wherein the enzyme medium is made according to the method steps of: (a) forming a seed culture by placing at least one fungus, a first carbon source, and a first nitrogen source in a container and agitating for about 72 hours at a temperature of from about 20° C. to about 35° C.; (b) transferring the contents of the seed culture to a fermentation vessel and adding a second carbon source, a second nitrogen source and water; (c) adjusting the pH of the contents of the fermentation vessel to a pH of from about 3 to about 5; (d) growing the fungus in the fermentation vessel; (e) collecting the product of step (d), which comprises a mixture of a solid waste material and an enzyme-containing liquid; (f) separating the solid waste material from the enzyme-containing liquid and collecting the enzyme-containing liquid; and (g) diluting the enzyme-containing liquid with water in a ratio of from about 5:1 to about 20:1 water to enzyme-containing liquid.

In some embodiments, the method of making a soy protein isolate may include any of the embodiments described above wherein the precipitated proteins are separated from the dissolved protein-containing liquid using a centrifuge. In some embodiments, the method of making a soy protein isolate may include any of the embodiments described above wherein the precipitated proteins are separated from the dissolved protein-containing liquid by filtration.

In some embodiments, the method of making a soy protein isolate may include any of the embodiments described above wherein the dissolved proteins in the dissolved protein-containing liquid are forced to precipitate out of solution by adjusting the pH of the monosaccharide-containing liquid to the isoelectric point of each one of the dissolved proteins and other biopolymers. In some embodiments, the method of making a soy protein isolate may include any of the embodiments described above wherein the pH of the dissolved protein-containing liquid is adjusted to be from about 4.3 to about 4.7.

In some embodiments, the method of making a soy protein isolate may include any of the embodiments described above wherein the dissolved proteins in the dissolved protein-containing liquid are forced to precipitate out of solution by diluting the monosaccharide-containing liquid with water or an aqueous solution. In some embodiments, the method of making a soy protein isolate may include any of the embodiments described above wherein the dissolved proteins and other biopolymers in the dissolved protein-containing liquid are forced to precipitate out of solution by the addition of ethanol.

In some embodiments, the method of making a soy protein isolate may include any of the embodiments described above and further comprises the step of adding an antimicrobial agent selected from the group consisting of sodium benzoate, benzoic acid, sodium azide, ethylenediaminetetraacetic acid (EDTA), and sodium nitrite to the mixture of step (a). In some embodiments, the method of making a soy protein isolate may include any of the embodiments described above and further comprises the step of heating the protein-containing material to a temperature of from about 155° C. to about 200° C. for a period of from about 30 minutes to 5 hours to reduce the growth of bacterial and other contaminants during hydrolysis.

In another aspect, the present invention is directed to a protein-containing powder made according to the methods set forth any of the embodiments described above. In another aspect, the present invention is directed to a liquid enzyme medium made according to the methods set forth any of the embodiments described above, wherein the liquid enzyme medium comprises at least one cellulase enzyme, at least one hemicellulase enzyme, and at least one pectinase enzyme. In another aspect, the present invention is directed to a soy-based monosaccharide-containing liquid made according to the methods set forth any of the embodiments described above. In another aspect, the present invention is directed to a soy protein isolate made according to the methods set forth any of the embodiments described above.

BRIEF DESCRIPTION OF THE DRAWINGS

For a more complete understanding of the features and advantages of the present invention, reference is now made to the detailed description of the invention along with the accompanying figures in which:

FIG. 1 is a graph showing the release of reducing sugars from solid soybean meal to the surrounding water along the protein separation and enrichment process using liquid enzyme media of different concentrations.

FIG. 2 is a schematic drawing for a simple laboratory flask used for enzymatic hydrolysis of soybean meal according to some embodiments of the present invention. The content in the flask is mixed by the whirling motion generated by a rotary shaker-incubator.

FIG. 3 is a graph showing time profiles of cellulase and xylanase production in fungal fermentation according to at least one embodiment of the present invention.

DETAILED DESCRIPTION OF THE ILLUSTRATIVE EMBODIMENTS

Figure 4:
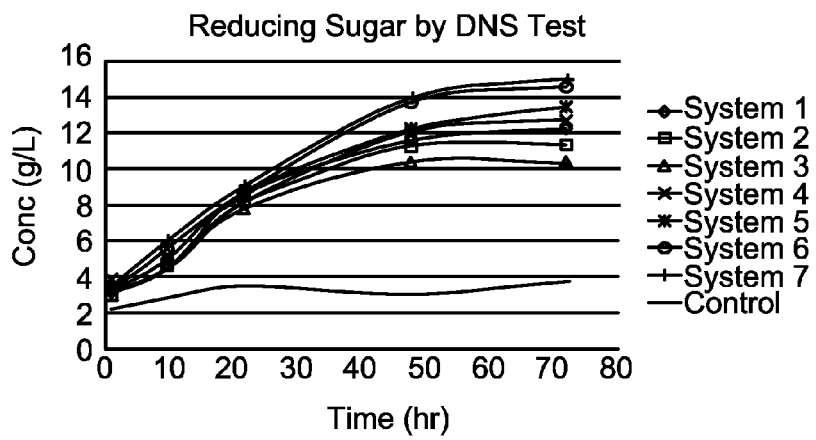
FIG. 4 is a graph showing reducing sugar concentration of hydrolysate measured by the dinitrosalicylic acid (DNS) assay according to at least one embodiment of the present invention.

The present invention is directed to enzyme based methods for separating protein from protein-rich materials derived from plant seeds, fruit, or other biomass and products made therefrom. The protein content in the resulting products is improved by separating and removing the carbohydrates from around the proteins in, for example, soybean meal. This removal is facilitated by the enzymatic hydrolysis of poly- and oligomeric carbohydrates into monosaccharides and other water soluble sugars. The present invention provides for the production of three streams of useful materials.

As set forth above, most soybean meal contains approximately 35% of carbohydrates, about 60% of which are non-starch polysaccharides (NSPs). Total non-starch polysaccharides are the sum of water soluble and water insoluble NSPs including cellulosic and non-cellulosic polysaccharides and pectic polymers. Stachyose, raffinose and verbascose are predominant among the oligosaccharides. All of these oligosaccharides are characterized by the presence of α-galactosidic bonds between galactose and other saccharides.

The smaller carbohydrates in the soybean meal, such as sucrose, are soluble in water and can, therefore, easily be removed from the protein containing material. However, the polysaccharides, such as cellulose, hemicellulose and pectin, and appreciable portions of oligosaccharides, such as raffinose and stachyose, are not so easily removed, as they may be trapped inside the complex structure of soybean meal. The concentration of these polysaccharides and oligosaccharides is an important consideration in the production and use of soy protein products. It is known that humans and other monogastric animals can hardly digest any of these carbohydrates due to the lack of α-galactosidase enzyme necessary to hydrolyze the α-galactosyl linkages present in carbohydrates like raffinose and stachyose. Instead, these components enter the lower intestinal tract where they may be metabolized by bacteria and/or fermented to produce intestinal gas causing considerable discomfort.

The protein content in the resulting products may be improved by separating and removing the carbohydrates (and other minor components) from in and around the proteins in, for example, soybean meal. This removal is facilitated by the enzymatic hydrolysis of poly- and oligomeric carbohydrates and other non-protein materials into monosaccharides and other water soluble sugars, referred to herein as soluble "total carbohydrates." Further, a significant amount of soluble protein and other materials are trapped within and around these oligosaccharides and polysaccharides. As these carbohydrates are broken down by enzyme hydrolysis into increasingly smaller sugars, it becomes easier for the larger trapped proteins to separate from the smaller saccharides.

The present invention provides for the production of three streams of useful materials. The first is an enriched protein material comparable in protein content to the SPCs of the prior art, containing the proteins remaining as solids at the process pH, fats, minerals, and other materials not hydrolyzed by the enzymes. Unlike the SPCs of the prior art, however, this enriched protein material does not have the significant quantities of indigestible oligosaccharides and polysaccharides. This material may be dried to a protein-rich powder or used in another form (e.g. a protein paste, protein mixture or protein solution). The second is an SPI made from the soluble protein in the hydrolysate. These enriched proteins (the enriched protein material and the SPI) are valuable for high-quality feed, food and industrial uses. The third stream is the soluble saccharides and hydrolyzed carbohydrates (releasing sugars) that can be converted by fermentation to various valuable bioproducts.

Accordingly, the present invention includes an enzyme based method for separating protein from a protein-rich or, at least, a protein-containing materials derived from plant seeds, fruit, or other biomass. While the protein material needed for germination is ordinarily contained in the seeds, as one of ordinary skill in the art will appreciate, there are plants that have very small seeds and store the protein needed for germination in the nearby fruit of the plant. Although the protein-rich material to be acted upon in the present invention is preferably derived from soy beans and is discussed herein in terms of soybean products, it should be understood that other similar protein-rich materials derived from plant seeds, such as wheat meal as well as fruit or other biomass, may also be used. In some embodiments, the protein-rich material may be defatted soybean meal, soy four, soy flakes, soybean powder or any combination thereof. In some embodiments, the protein-rich material may be defatted soy meal. In some embodiments, the protein-rich material may be soy flour. In some embodiments, the protein-rich material may be defatted soy flakes. In some embodiments, the protein-rich material may be defatted soy powder.

The protein-containing material may also be heated or irradiated by any methods known in the art before being processed to eliminate bacteria and other contamination. As one of ordinary skill will understand, the protein-containing material should be heated to a temperature above the heat tolerances of the contaminating microorganisms and spores and for a duration which is sufficient to kill the microorganisms and spores, without significantly degrading the proteins in the protein-containing material. It has been found that heating the protein-containing material to a temperature of at least 150° C. for a period of from 30 minutes to about 5 hours depending upon the heat penetration into the protein-containing material, may significantly reduce the presence of contaminating microorganisms. In some embodiments, the protein-containing material may be heated to at least 160° C. In some embodiments, the protein-containing material may be heated to at least 170° C. In some embodiments, the protein-containing material may be heated to at least 180° C. In some embodiments, the protein-containing material may be heated to 160° C. for about 2 hours. In some embodiments, the protein-containing material may be heated to 170° C. for about 2 hours. In some embodiments, the protein-containing material may be spread thin and heated to maximize heat penetration. In some embodiments, the protein-containing material may be heated using microwave or infrared. It should also be appreciated however, that while this process significantly reduces or substantially eliminates contamination by microorganisms at the beginning of the process, care must be taken to ensure that the protein-containing material does not become contaminated later in the process.

The soybean meal or other protein-rich material is added to a liquid enzyme medium or broth prepared using one or more fungi and comprising at least one cellulase, at least one hemicellulase, preferably xylanase, and at least one pectinase, (which may be prepared as set forth below) in a suitable vessel. Suitable vessels for hydrolysis are any containers that can hold the weight of liquid enzyme medium and soybean meal and do not release harmful substances, for example, due to leaching, degradation or corrosion, into the vessel content, including but not limited to vessels made of stainless steel, glass, hard plastics, and pretreated wood. The content needs to be maintained at desired pH and temperature ranges and be properly mixed. pH control can be achieved by use of buffer and/or addition of acid or base, triggered by periodic measurement of sample pH or continuous real-time monitoring of pH of vessel content with pH probe(s). Temperature control can be achieved by placing the vessel in a temperature-controlled space/room and/or by heating and cooling jackets and/or heat-exchange coils/structures in contact with the mixed vessel content. For small-scale operations, the mixing can be achieved easily by a shaker. For large-scale operations, the mixing may be more effectively done by in-vessel mechanical mixers/agitators. In some embodiments, the enzyme hydrolysis vessel is a stainless steel vessel equipped with in-vessel mechanical mixer, pH probe, temperature probe, in-vessel heat-exchange plates or coils, and automatic acid/base addition for pH control and automatic heating/cooling for temperature control.

The liquid enzyme medium or enzyme broth is made by fermentation of an appropriate substrate by one or more fungi capable of producing at least one cellulase, at least one hemicellulase, preferably xylanase, and/or at least one pectinase under the proper conditions. It is well known in the art, for example, that cellulose, which is contained in soy products, can be hydrolyzed into its component sugars by a well known group of cellulase enzymes. It is likewise known that some fungi, such as *Trichoderma reesei*, can, depending on the culture conditions, inducers and substrates, produce these cellulase enzymes effectively. Cellulase enzymes fall into three major classes: endo-glucanases, exo-glucanases and β-glucosidases and it should be understood that the enzymatic degradation of cellulose to small sugars is accomplished by the synergistic action of these three groups of enzymes. This degradation requires at least the following steps: cellulase adsorption onto the surface of the cellulose, breakdown (by hydrolysis) of cellulose to increasingly smaller sugar molecules, and desorption of the cellulase.

In addition, it has been found that various other enzyme mixtures including cellulase, hemicellulase (includes xylanase, mannanase, α-galactosidase, α-arabinosidase, β-xylosidase and acetyl xylan esterase), pectinase (including protopectinases, esterases and depolymerases such as pectinesterase, polygalacturonase, galacturan 1,4-α-galacturonidase, exo-poly-α-galacturonosidase, pectate lyase, pectate disaccharide-lyase, oligogalacturonide lyase and pectin lyase), phytase, phosphatase, and nuclease can be produced by adjusting the production processes, media and fungal species. Use of proper enzyme mixtures can hydrolyze the polysaccharides, oligosaccharides, and other undesirable polymers in soybean meal to allow effective and economical separation, enrichment and/or purification of soy proteins for industrial applications.

As set forth above, any fungi known or unknown that will produce a cellulase, hemicellulase, and/or pectinase in the presence of the selected substrate may be used. A single species and/or strain of fungus or multiple species and/or strains of fungi may be used but, the liquid enzyme medium or broth prepared should have at least one cellulase enzyme, at least one hemicellulase enzyme, preferably xylanase, and at least one pectinase enzyme. Fungi that may be used include, but are not limited to the genera, *Trichoderma, Aspergillus, Penicillium, Saccharomyces, Phanerochaete, Rhizopus, Fusarium, Neurospora, Podospora, Pichia,* and *Schizophyllum*.

Fungal species and strains that may be used include, but are not limited to, *Trichoderma reesei* Rut-C30 NRRL 11460, *Aspergillus niger* NRRL 322, *Aspergillus niger* NRRL 325, *Aspergillus niger* NRRL 328, *Aspergillus niger* NRRL 334, *Aspergillus niger* NRRL 341, *Aspergillus niger* NRRL 348, *Aspergillus niger* NRRL 363, *Aspergillus niger* NRRL 566, *Aspergillus niger* NRRL 599, *Aspergillus niger* NRRL 2270, *Aspergillus niger* NRRL 13201, *Aspergillus niger* NRRL 13219, *Aspergillus niger* NRRL 62517 and *Aspergillus aculeatus* NRRL 2053. These fungi may be obtained through the Agricultural Research Service (ARS) at the U.S. Department of Agriculture.

In some embodiments, the liquid enzyme medium or enzyme broth is made by fermentation of an appropriate substrate by *Aspergillus niger* NRRL 322. In some embodiments, the liquid enzyme medium or enzyme broth is made by fermentation of an appropriate substrate by *Aspergillus niger* NRRL 341. In some embodiments, the liquid enzyme medium or enzyme broth is made by fermentation of an appropriate substrate by *Trichoderma reesei* Rut-C30 NRRL 11460.

The liquid enzyme medium or enzyme broth for use in the hydrolysis of the polysaccharides and oligosaccharides in soybean meal is made by first forming a seed culture or preculture by placing at least one fungus (as described above), a suitable substrate and water in a shakable container. The substrate should be both sustaining the fungi and inducing it to produce the enzymes necessary for hydrolysis including, but not limited to, a cellulase, a hemicellulase and a pectinase. The substrate should include at least one carbon source and at least one nitrogen source and at least one inducer, which may be one or both of the carbon source and the nitrogen source or a different substance. As used herein, an inducer is any substrate or other substance that induces fungi to produce enzymes for hydrolysis of carbohydrates.

While not required to practice the present invention, the substrate may be varied with the material to be hydrolyzed. If the fungi properly selected, it will produce the enzymes necessary to consume the substrate upon which it feeds and may produce, in addition to the cellulases, hemicellulases, and pectinases discussed above, other auxillary enzymes that will facilitate the effective consumption of the substrate. In some embodiments the substrate may be the protein-containing material to be hydrolyzed.

Any carbon source capable of being consumed by the fungus in the seed culture may be used provided that one or more of the carbon source and the nitrogen source or some other initiator are capable of inducing production of enzymes for hydrolysis of the desired protein-containing material. Suitable carbon sources may include, but are not limited to, soy hulls, potato dextrose, sucrose, lactose, Avicel, glucose, fructose, maltose, glycerol, the hydrolysate from the enzyme hydrolysis process, other soluble soy carbohydrates, and other carbohydrates, proteins, fats, fatty acids, lipids or combinations thereof. In some embodiments, the carbon source may be soy hulls. In some embodiments, the carbon source may be sucrose. In some embodiments, the carbon source may be a mixture of soy hulls and sucrose. In some embodiments, the carbon source may be a potato dextrose.

Likewise, any nitrogen source capable of being consumed by the fungus in the seed culture may be used again provided that one or more of the carbon source and the nitrogen source or some other initiator are capable of inducing production of enzymes for hydrolysis of the desired protein-containing material. Suitable nitrogen sources may include, but are not limited to, from (1) organic nitrogen-containing materials such as proteins, nucleic acids, corn steep liquor, milk, dairy products and waste, peptides, amino acids, yeast extract, tryptone, peptone, other protein digests (including the proteins present in the hydrolysate generated from the enzyme hydrolysis process), and urea; (2) inorganic nitrogen-containing materials particularly ammonia, various ammonium salts (for example, ammonium sulfate, ammonium chloride, and ammonium phosphate) and various nitrates (for example, sodium nitrate, ammonium nitrate, potassium nitrate, calcium nitrate, magnesium nitrate, and nitric acid); and (3) mixtures of the above organic and inorganic nitrogen-containing materials. More specifically, the nitrogen source may include, without limitation, soybean meal, soy flour, corn steep liquor, dairy waste containing milk protein, a mixture of from about 0 g/L to about 2.65 g/L of Ammonium Sulfate, from about 0 g/L to about 0.3 g/L of urea, and from about 0 g/L to about 3.47 g/L of Proteose peptone, or combinations thereof. In some embodiments, the nitrogen source may be defatted soy flour. In some embodiments, the nitrogen source may be a mixture of about 1.4 g/L of ammonium sulfate, about 0.3 g/L of urea, and about 1 g/L of Proteose peptone.

The seed culture is shaken or otherwise agitated using any method known in the art for that purpose for a period of from about 12 hours to about 96 hours at a temperature of from about 15° C. to about 50° C. and a pH of from about 3 to about 6 depending upon the suitable growth and enzyme production temperature for the fungal strain used. As will be appreciated by those of skill in the art, the seed culture should be used when it has grown to a culture stage between late exponential-growth phase and the early stationary phase. Generally, this is the stage at which the culture has about the highest cell concentration, while being still active. If the seed culture is harvested too early, the seed concentration will be too low. If harvested too late, the culture will have been non-growing for too long and will need time for reactivation after having been added as seeds to the fermentor. The time to reach this suitable stage will vary with the actual process conditions including, but not limited to, the strain, medium, temperature, pH, and dissolved oxygen concentration. In some embodiments, the seed culture is allowed to ferment for a period of from between about 48 and about 72 hours. In some embodiments, the seed culture is allowed to ferment for a period of about 72 hours. In some embodiments, the seed culture may be fermented at a temperature of from about 28° C. to about 30° C. In some embodiments, the seed culture may be fermented at a temperature of 28° C. In some embodiments, the seed culture has a pH of from about 5 to about 6. In some embodiments, the seed culture has a pH of from about 4 to about 5. In some embodiments, the seed culture has a pH of 4.8.

In another embodiment, the seed culture or preculture is prepared by incubating at least one fungus (as described above) in a potato dextrose broth by inoculating loops of culture maintained on potato dextrose agar plates at 4° C.

After incubating for a suitable amount of time as set forth above (usually about 72 hours) the contents of the seed culture are then transferred to a fermentation vessel as described above, to which a second carbon source, a second nitrogen source, and water are again added. As with the substrate used for the seed culture, the substrate for the fermentation vessel must both sustain the fungi and induce it to produce the enzymes necessary for hydrolysis including, but not limited to, a cellulase, a hemicellulase and a pectinase. Enzyme production may be induced by any one or all of the second carbon source, the second nitrogen source, or another material. The second carbon source may be any of the carbon sources set forth above with respect to the seed culture and may be the same as the carbon source used for the seed culture. In some embodiments, the second carbon source may be soy hulls. In some embodiments, the second carbon source may be sucrose. In some embodiments, the second carbon source may be a mixture of soy hulls and sucrose.

The second nitrogen source may be any of the nitrogen sources set forth above with respect to the seed culture and may be the same as the nitrogen source that was used for the seed culture. In some embodiments, the nitrogen source may be defatted soy flour. In some embodiments, the nitrogen source may be a mixture of about 1.4 g/L of ammonium sulfate, about 0.3 g/L of urea, and about 1 g/L of Proteose peptone.

The pH of the fermentation mixture is then adjusted to be from about 3 to about 8 by the addition of a NaOH and HCl. In some embodiments, the fermentation mixture has a pH of from about 3.5 to about 5. In some embodiments, the fermentation mixture has a pH of 4.8.

To facilitate further fermentation by increasing air flow and food distribution and extending the life of the fungi, the mixture is continuously mixed and/or agitated and air and/or oxygen are pumped into the fermentation vessel. The mixture may be mixed and/or agitated by any method known in the art including, but not limited to stirring, agitating, shaking (on a shaker table), tumbling, or kneading. In some embodiments, the mixture may be agitated by turbines, impellers and/or propellers. In some embodiments, the shaker speed is about from 100 rpm to 350 rpm for shaker study. In some embodiments, the speed of stirring plate is about 300 rpm to 500 rpm. In some embodiments, the three-blade marine propeller or six-blade disk turbine are applied to fermentation vessels stirring, and the agitation speed is about from 100 rpm to 400 rpm. Preferably, the dissolved oxygen concentration of the material in the fermentation vessel is maintained above about 20%, but this is not required. In some embodiments, the dissolved oxygen concentration of the material in the fermentation vessel is maintained above about 5%. In some embodiments, the dissolved oxygen concentration of the material in the fermentation vessel is maintained above about 10%. In some embodiments, the dissolved oxygen concentration of the material in the fermentation vessel is maintained above about 15%.

The mixture is left to ferment until enzyme production has substantially stopped at which time it is usually apparent that the fungi have used up the substrate and the pH has started to rise due to endogenous metabolism. This process usually takes from about 2 days to about 6 weeks. In some embodiments, the mixture is allowed to ferment for a period of from about 2 days to about 2 weeks. In some embodiments, the mixture is allowed to ferment for a period of from about 2 days to about 1 week. In some embodiments, the mixture is allowed to ferment for a period of from about 2 days to about 3 days.

The mixture may be allowed to ferment at a temperature of from about 20° C. to about 50° C. to facilitate fermentation. In some embodiments, the mixture is allowed to ferment a temperature of from about 28° C. to about 30° C.

After fermentation is substantially complete, the mixture is then collected. Although not always required, in some embodiments, the solid material is separated from the enzyme-rich liquid by any means known in the art including, but not limited to, spinning in a centrifuge, settling by gravity, or filtration.

In some embodiments the method further includes the step of diluting the enzyme-rich mixture or liquid obtained above with water or an aqueous solution in a ratio of from about 1:1 to about 50:1 water (or aqueous solution) to enzyme-rich mixture or liquid. In some embodiments, the enzyme-rich mixture or liquid may be diluted with water to a ratio of from about 5:1 to about 30:1 water (or aqueous solution) to enzyme-rich mixture or liquid. In some embodiments, the enzyme-rich mixture or liquid may be diluted with water (or aqueous solution) to a ratio of from about 5:1 to about 20:1 water to enzyme-rich mixture or liquid In some embodiments, the enzyme-rich mixture or liquid may be diluted with water (or aqueous solution) to a ratio of from about 5:1 to about 8:1 water (or aqueous solution) to enzyme-rich mixture or liquid In some embodiments, the enzyme-rich mixture or liquid may be diluted with water (or aqueous solution) to a ratio of about 5:1 water (or aqueous solution) to enzyme-rich mixture or liquid. The pH of the diluted enzyme-rich mixture or liquid is then adjusted to a pH of from about 4 to about 6 for use in hydrolysis as set forth above. In some embodiments, the pH of the diluted enzyme-rich mixture or liquid may be adjusted to a pH of from about 4.8 to about 5.0 before its use for hydrolysis. In some embodiments, the pH of the diluted enzyme-rich mixture or liquid may be adjusted to a pH of about 4.8.

The liquid enzyme medium so produced, and used for hydrolysis as set forth herein may contain a significant amount of solid material.

As set forth above, the liquid enzyme medium is then mixed with soy meal or other protein-rich material in a vessel suitable for the hydrolysis. Such vessels are any containers that can hold the weight of liquid enzyme medium and soybean meal and do not release harmful substances, for example, due to leaching, degradation or corrosion, into the vessel content, including but not limited to vessels made of stainless steel, glass, hard plastics, and pretreated wood. The content needs to be maintained at desired pH and temperature ranges and be properly mixed. pH control can be achieved by use of buffer and/or addition of acid or base, triggered by periodic measurement of sample pH or continuous real-time monitoring of pH of vessel content with pH probe(s). Temperature control can be achieved by placing the vessel in a temperature-controlled space/room and/or by heating and cooling jackets and/or heat-exchange coils/structures in contact with the mixed vessel content. For small-scale operations, the mixing can be achieved easily by a shaker. For large-scale operations, the mixing may be more effectively done by in-vessel mechanical mixers/agitators. In some embodiments, the enzyme hydrolysis vessel is a stainless steel vessel equipped with in-vessel mechanical mixer, pH probe, temperature probe, in-vessel heat-exchange plates or coils, and automatic acid/base addition for pH control and automatic heating/cooling for temperature control.

It has been found that, in general, the greater the strength of the enzyme broth the more sugars will be released (See FIG. 1) as a function of time. As one of ordinary skill in the art will appreciate, however, this relationship is not linear and the amount of additional sugars released by an increase in the strength of the enzyme broth steadily decreases as additional sugars are released. Accordingly, there is a point of diminishing returns where the value of the additional sugars released does not justify the additional time and expense involved in fermenting the additional enzyme broth. Accordingly, the ratio of the liquid enzyme medium to the protein-rich material is generally from about 3:1 to about 10:1, volume to weight, depending upon the protein rich material used and the concentration of the liquid enzyme medium used. In addition, if too much protein rich material is added, the mixture may become highly viscous and difficult in not impossible to stir or agitate. In some embodiments, the ratio of the liquid enzyme medium to the protein-rich material may be from about 3:1 to about 5:1. In some embodiments, the ratio of the liquid enzyme medium to the protein-rich material may be about 4:1.

The hydrolysis mixture may also include an antimicrobial agent to reduce microbial contamination. Suitable antimicrobial agents are known in the art and include, but are not limited to, sodium benzoate, benzoic acid, sodium azide, ethylenediaminetetraacetic acid (EDTA), and sodium nitrite.

The hydrolysis mixture may also include a buffer. Suitable buffers may include, without limitation, citrate buffers, acetate buffers, phosphate buffers, MES (2-(N-morpholino)ethanesulfonic acid) buffers, succinic acid buffers, and combinations of the above. In some embodiments, the buffer may be a citrate buffer for a pH of 4.8. The mixture should be kept at a pH of from about 4 to about 6 and preferably from about 4.8 to about 5.0. The pH may be adjusted by means of the buffer described above and/or by adding NaOH or HCl. In some embodiments, the pH may be kept at 4.8.

A schematic drawing for an enzymatic hydrolysis of soybean meal according to some embodiments of the present invention is shown in FIG. 2.

The mixture is then stirred or otherwise agitated at a temperature of from about 45° C. to about 50° C. to facilitate hydrolysis by the enzymes in the liquid enzyme medium of the polysaccharides, oligosaccharides, and other undesirable polymers in the soy meal or other protein-containing material being used. In some embodiments, the mixture is stirred or otherwise agitated at a temperature of from about 48° C. to about 50° C. In some embodiments, the mixture is stirred or otherwise agitated at a temperature of about 50° C.

The mixture is then stirred or otherwise agitated for a period of from about 1 hour to about 96 hours to facilitate hydrolysis. One of ordinary skill in the art will be able to determine the point at which hydrolysis is substantially complete from monitoring the concentration of releasing sugars in the mixture and comparing it to a maximum possible concentration calculated based upon the known carbohydrate composition of the volume of soy meal or other protein-rich material being hydrolyzed. As should also be apparent, hydrolysis may be substantially complete when there is little or no increase in the concentration of releasing sugars in the hydrolysis mixture. Further, in optimized and standardized operation, substantial completion of hydrolysis may also be judged by other properties such as mixture viscosity, color, etc.

However, in applications where there is no need for the carbohydrates in the mixture to be fully or even substantially hydrolyzed, the hydrolysis may be deemed substantially complete and stopped at any point. In some embodiments, hydrolysis is deemed to be substantially complete when the concentration of total carbohydrate reaches or exceeds about 50% of the maximum possible concentration calculated based upon the known carbohydrate composition of the volume of soy meal or other protein-rich material being hydrolyzed. In some embodiments, hydrolysis is deemed to be substantially complete when the concentration of total carbohydrate reaches or exceeds about 60% of the maximum possible concentration calculated based upon the known carbohydrate composition of the volume of soy meal or other protein-rich material being hydrolyzed. In some embodiments, hydrolysis is deemed to be substantially complete when the concentration of total carbohydrate reaches or exceeds about 70% of the maximum possible concentration calculated based upon the known carbohydrate composition of the volume of soy meal or other protein-rich material being hydrolyzed. In some embodiments, hydrolysis is deemed to be substantially complete when the concentration of total carbohydrate reaches or exceeds about 80% of the maximum possible concentration calculated based upon the known carbohydrate composition of the volume of soy meal or other protein-rich material being hydrolyzed. In some embodiments, hydrolysis is deemed to be substantially complete when the concentration of total carbohydrate is between about 90% and about 100% of the maximum possible concentration calculated based upon the known carbohydrate composition of the volume of soy meal or other protein-rich material being hydrolyzed.

In some embodiments, the mixture is stirred or otherwise agitated for a period of from about 1 hours to about 96 hours. In some embodiments, the mixture is stirred or otherwise agitated for a period of from about 4 hours to about 48 hours. In some embodiments, the mixture is stirred or otherwise agitated for a period of from about 8 hours to about 48 hours. In some embodiments, the mixture is stirred or otherwise agitated for a period of about 48 hours.

As set forth above, if in the single batch system described above, too much protein rich material is added, the mixture may become highly viscous and difficult in not impossible to stir or agitate. This can significantly limit the amount of protein-rich material that can be processed by a single batch of liquid enzyme medium. To avoid this limitation, a multiple batch process may be used. It has been found that while the mixture is highly viscous when hydrolysis begins, as the carbohydrates in the protein-rich material are broken down into increasingly smaller sugars and eventually to soluble monosaccharides and other small sugars, the mixture becomes less and less viscous. Eventually, the viscosity drops to the point where it becomes possible to add additional batches of protein rich material without increasing the viscosity of the mixture to the point that it is difficult in not impossible to stir or agitate. This process may be repeated to add multiple batches of protein-rich material to the mixture. If required, additional liquid enzyme medium and/or water may also be added. The amount of time it takes for the for the viscosity of the mixture to drop to the point where additional protein rich material may be added will, of course, depend upon the processing conditions but one of ordinary skill in the art will be able to determine when addition protein-rich material may be added and in what amounts. Some advantages of the multiple batch processing method are that it maximizes the utility of the enzymes in the liquid enzyme medium and that the concentrations of soluble proteins and soluble saccharides in the hydrolysate are far higher than they would be for a comparable single batch process. This, in turn, leads to the production of more concentrated SPIs and saccharide-rich liquids in later processing steps, as set forth below.

After hydrolysis is substantially complete, the resulting mixture will have a solid component made up of solid proteins and any remaining insoluble material and a liquid hydrolysate component made up of the soluble sugars, including the soluble saccharides produced during hydrolysis, soluble proteins, and other water soluble and colloidal materials. The solid component may be separated from the liquid hydrolysate component by any means known in the art including with out limitation a centrifuge, filtration, membrane-filtration, dialysis and/or electrodialysis. In some embodiments, the mixture is then spun in a centrifuge or filtered to separate the solid protein-rich component material from the saccharide-rich liquid component. In some embodiments, the method further comprises the step of removing the liquid component and drying the solid protein-rich component to form a protein-rich powder. In some embodiments the protein-rich solid component is reduced to a paste. In some embodiments the protein-rich solid component is a mixture or a colloid or may be re-dissolved into a solution.

The solid protein-rich material generated using the method set forth above is a substantial improvement over the SPCs known in the art because depending upon the degree of hydrolysis, the amount of indigestible oligosaccharides and polysaccharides is greatly reduced or substantially eliminated. Moreover, the protein yield is comparable, if somewhat less than known SPCs, without the negative effects on the proteins that can come from an ethanol or acid wash. And while the protein yield at this point in the process may be lower than conventional SPC, this is because hydrolysis of the indigestible oligosaccharides and polysaccharides into smaller saccharides frees soluble proteins that are bound up with and/or trapped by or within those oligosaccharides and polysaccharides. While these soluble proteins do not become part of the solid protein-rich material captured at this stream (thus reducing the protein yield), these soluble proteins are later captured from the liquid hydrolysate component to form an SPI, as described below.

Another aspect of the present invention is directed to methods of further processing the liquid hydrolysate byproduct (the liquid hydrolysate component described above) produced into a commercially valuable SPI and a commercially valuable saccharide-rich liquid. The SPI is created by separating the soluble proteins from the saccharide-rich liquid in the liquid hydrolysate byproduct by any means known in the art for that purpose and then collecting the proteins. Strategies for separating the soluble proteins from the saccharide-rich liquid in the liquid hydrolysate byproduct include filtering out the larger protein molecules from the smaller saccharide molecules by such techniques as membrane filtration, dialysis, or electrodialysis or by forcing the proteins to precipitate out of solution by such techniques as, for example, heat-induced precipitation, salt-induced precipitation, and/or solvent-induced precipitation. The remaining liquid is the commercially valuable saccharide-rich liquid, for use in fermentation and the like.

As set forth above, the soluble proteins in the liquid hydrolysate byproduct can be forced to precipitate out of solution by any means known in the art. Suitable methods include without limitation, heating, adjusting the pH to the isoelectric point for the proteins, and dilution with water to force the proteins out of solution. In some embodiments, the proteins in the liquid hydrolysate byproduct are forced to precipitate out of solution by heating the liquid hydrolysate byproduct to a temperature of from about 60° C. to about 100° C. In some embodiments, liquid byproduct of the process described above is heated to a temperature of from about 80° C. to about 100° C. In some embodiments, liquid byproduct of the process described above is heated to a temperature of about 95° C.

In some embodiments, the proteins in the liquid hydrolysate byproduct are forced to precipitate out of solution by adjusting the pH of the liquid hydrolysate byproduct to the isoelectric points of the various dissolved proteins, which generally fall within a pH range of from about 4.3 to about 5.5. The pH is adjusted through the pH range and as the pH of a particular dissolved protein is reached, that protein will precipitate out of solution and may be collected. In some embodiments, the pH of the liquid hydrolysate byproduct is adjusted over the pH range of from about 4.3 to about 5.0 to precipitate out the dissolved proteins. In some embodiments, the pH of the liquid hydrolysate byproduct is adjusted over the pH range of from about 4.3 to about 4.7 to precipitate out the dissolved proteins.

In some embodiments, the proteins in the liquid hydrolysate byproduct are forced to precipitate out of solution by diluting the liquid hydrolysate byproduct with water or an aqueous solution until the dissolved proteins come out of solution. In some embodiments, the liquid hydrolysate byproduct is diluted with water in a ratio of 10:1 water to liquid hydrolysate byproduct. The method, however, significantly dilutes the commercially valuable saccharide-rich liquid and is not preferred where the saccharide-rich liquid is intended for further use.

In some embodiments, the proteins in the liquid hydrolysate byproduct are forced to precipitate out of solution by addition of ethanol. (See Example 9) In some embodiments, the ethanol is added to the liquid hydrolysate byproduct in an ethanol to liquid hydrolysate byproduct volume ratio of from 1:5 to 2:1. In some embodiments, the ethanol is added to the liquid hydrolysate byproduct in a 1:1 volume ratio.

Once the proteins have come out of solution they may be removed from the liquid hydrolysate byproduct by any method known in the art. In some embodiments, the precipitated protein may be removed from the liquid hydrolysate byproduct by spinning the liquid hydrolysate byproduct in a centrifuge wherein the precipitated proteins may be collected as an SPI and/or the saccharide-rich liquid collected for use in other processes. In some embodiments, the solid SPI and saccharide-rich liquid in the liquid hydrolysate byproduct may be separated by filtration.

The SPI produced by this method is comparable to other SPIs known in the art, but may have a larger protein yield because of the additional soluble proteins released into solution by the hydrolysis of the oligosaccharides and polysaccharides into smaller sugars.

If desirable, the saccharide-rich liquid produced by this method may be processed in an autoclave to denature any remaining enzymes and eliminate any microbial contamination.

The saccharide-rich liquid produced according to the present invention has a wide variety of commercial uses including, but not limited to, fermentation to produce other bioproducts such as arabitol and other sugar derivatives, enzymes, xanthan gums, alginates, microbial polyesters such as polyhydroxyalcanoates and other biopolymers, rhamnolipids, sophorolipids and other biosurfactants, succinic acid, citric acid and other organic acids, pharmaceuticals including antibiotics, specialty chemicals, lipids, nutritional compounds, products from heterotrophic algae, and bioethanol.

As set forth above, an antimicrobial agent such as sodium azide, ethylenediaminetetraacetic acid (EDTA), benzoate, benzoic acid or sodium nitrite may be added after the liquid enzyme medium has been produced and collected from the fermentation to prevent contamination by bacteria or other microorganisms during the storage and enzyme hydrolysis process. After the enzyme hydrolysis, the benzoate remains soluble in the liquid hydrolysate byproduct and must be removed before the liquid hydrolysate byproduct (or the saccharide-rich liquid) can be used for other types of fermentation. In some embodiments, the benzoate/benzoic acid may be removed from the hydrolysate by extraction with a solvent such as butanol, methanol, propanol, acetone, tetrahydrofuran or a combination thereof. In some embodiments, the benzoate/benzoic acid may be removed from the liquid hydrolysate byproduct by extraction with butanol. In some other embodiments, the sodium benzoate, sodium nitrite, benzoic acid sodium azide, ethylenediaminetetraacetic acid (EDTA), or other antimicrobial agent may be removed from the liquid hydrolysate byproduct by filtration through granulated activated carbon.

The above removal process can be avoided if the protein-containing material is sterilized by dry heating, autoclaving or other thermal, chemical or irradiation-based sterilization methods. If the sterilization approach is taken, the remainder of the enzyme hydrolysis process must be done under sterile conditions to prevent recontamination. That means that the reactor needs to be sterilized (e.g., by autoclaving) and the liquid enzyme medium, when harvested from the fermentation, has to be harvested under conditions not allowing the introduction of contaminating microorganisms.

In some embodiments, the present invention may include a method of making a soy-based monosaccharide-rich liquid for use in fermentation comprising the steps of: (a) placing soybean meal in a container; (b) preparing an enzyme solution comprising at least one cellulase, at least one hemicellulase, and at least one pectinase wherein said enzyme solution has a pH of from about 4.6 to about 5.2; (c) combining the enzyme solution of step (b) and the soybean meal material of step (a); (d) stirring the mixture of step (c) at a temperature of from about 45° C. to about 50° C. for a period of from about 12 hours to about 48 hours; (e) spinning the resulting mixture in a centrifuge to separate the solid material from the monosaccharide-rich liquid; (f) removing the monosaccharide-rich liquid and heating it to a temperature of from about 60° C. about 100° C. to precipitate out the remaining proteins; (g) spinning the resulting mixture in a centrifuge to separate the solid material from the monosaccharide-rich liquid; and (h) collecting the monosaccharide-rich liquid.

In some embodiments, the present invention may include a method of making a soy protein isolate comprising the steps of: (a) placing soybean meal in a container; (b) preparing an enzyme solution comprising at least one cellulase, at least one hemicellulase, and at least one pectinase wherein said enzyme solution has a pH of from about 4.6 to about 5.2; (c) combining the enzyme solution of step (b) and the protein-containing soybean meal material of step (a); (d) stirring the mixture of step (c) at a temperature of from about 45° C. to about 50° C. for a period of from about 12 hours to about 48 hours; (e) spinning the resulting mixture in a centrifuge to separate the solid material from the monosaccharide-rich liquid; (h) removing the monosaccharide-rich liquid and heating it to a temperature of from about 60° C. to about 100° C. in order to precipitate out the remaining proteins; (i) spinning the resulting mixture in a centrifuge to separate the almost pure, solid protein from the liquid; (j) removing the monosaccharide-rich liquid; and (k) collecting the soy protein isolate.

In some embodiments, the present invention may include a method of producing and avoiding contamination of an enzyme solution comprising the steps of: (a) forming a seed culture by placing at least one fungus, a carbon source selected from the group consisting of soy hulls and sucrose, a nitrogen source selected from the group consisting of soy flour and a mixture of from about 0 g/L to about 2.65 g/L of ammonium sulfate, from about 0 g/L to about 0.3 g/L of urea, and from about 0 g/L to about 3.47 g/L of Proteose peptone in a container and agitating for about 72 hours at a temperature of from about 28° C. to about 30° C.; (b) transferring the contents of the seed culture to a fermentation vessel and adding a carbon source selected from the group consisting of soy hulls and sucrose, a nitrogen source selected from the group consisting of soy flour and a mixture of from about 1.4 g/L to about 7 g/L of ammonium sulfate, from about 0 g/L to about 1 g/L of urea, and from about 0 g/L to about 3 g/L of Proteose peptone, and water; (c) adjusting the pH of the fermentation vessel to from about 3 to about 6 and allowing it to ferment until enzyme production is substantially complete; (d) separating and removing the enzyme-containing liquid and diluting it from about 5:1 to about 10:1 with water to form the liquid enzyme medium; (e) adding sodium benzoate or benzoic acid to the liquid enzyme medium to reduce contamination; (f) using the liquid enzyme medium to hydrolyze carbohydrates in a protein-containing material derived from plant seeds, fruits or other biomass; and (g) removing said sodium benzoate or benzoic acid using activated carbon filtration.

As should be apparent, the method of the present invention allows for the production of a range of soy protein products with different protein contents, all having high protein yields (similar to those of the current commercial SPC production processes and much higher than those of the current commercial SPI production processes). The protein separation, enrichment and/or purification processes of the present invention are very simple, similar to those of the current commercial SPC production processes based on wash with water of isoelectric pH, and much simpler than those of the current commercial SPI production processes. Simply put, this invention leads to processes that are as simple as the current SPC processes and capable of producing soy protein products with protein contents and purities as high as those of current SPI.

For example, aquaculture feed can be an important target use of the enriched soy proteins. Global demand for seafood is growing rapidly and more than 40% of the demand is met by aquaculture. Production of fish meal, the conventional protein source for aquaculture feed, has reached the maximum capacity allowable by sustainable fishing. Fish meal has higher protein contents (70%) than soybean meal (50%). With the new enzymatic method, we have effectively enriched soybean meal to 80%-90% proteins. Further, with the hydrolysis of hemi/celluloses, the enzyme-enriched soy proteins are expected to reduce any indigestion concerns.

In light of the foregoing, it should be appreciated that the present invention significantly advances the art by providing a method of separating protein from protein-containing material derived from plant seeds that is structurally and functionally improved in a number of ways. While particular embodiments of the invention have been disclosed in detail herein, it should be appreciated that the invention is not limited thereto or thereby inasmuch as variations on the invention herein will be readily appreciated by those of ordinary skill in the art. The scope of the invention shall be appreciated from the claims that follow.

EXAMPLES

The following examples are offered to more fully illustrate the invention, but are not to be construed as limiting the scope thereof. Further, while some of examples may include conclusions about the way the invention may function, the inventors do not intend to be bound by those conclusions, but put them forth only as possible explanations. Moreover, unless noted by use of past tense, presentation of an example does not imply that an experiment or procedure was, or was not, conducted, or that results were, or were not actually obtained. Efforts have been made to ensure accuracy with respect to numbers used (e.g., amounts, temperature), but some experimental errors and deviations may be present. Unless indicated otherwise, parts are parts by weight, molecular weight is weight average molecular weight, temperature is in degrees Centigrade, and pressure is at or near atmospheric.

Example 1

For example, we produced the enzymes by submerged fermentation of *T. reesei* Rut-C30 NRRL 11460, a reported cellulase producer. A set of possible procedures are described in the following: A preculture was prepared in potato dextrose broth by inoculating loops of culture maintained on potato dextrose agar plates at 4° C. After 72 hours of incubation, the preculture was used to inoculate a submerged fermentation vessel. The cells were permitted to grow on defatted soy flour as the nitrogen source and lactose, soluble soy carbohydrates, or soybean hull as the carbon source.

The pH of seed culture broth is kept at a set range for good cell growth and enzyme production and the dissolved oxygen concentration in the broth is maintained above 20%. After growing the fungus for 6 days to 2 weeks, the cells were separated from the fermentation broth by filtration. The broth was found to contain cellulase, hemicellulase and pectinase (among others), which can then be added to soy meal for enrichment of proteins. The production profiles of cellulase (activity evaluated in Filter Paper Units) and hemicellulase (evaluated as xylanase) of a batch of *T. reesei* fermentation with soy meal and Avicel (commercial, purified cellulose) as the nitrogen and carbon substrates are shown in FIG. 3.

Example 2

Enzyme Hydrolysis of Soybean Meal with Different Enzyme Activity Levels

Objective of this experiment was to evaluate the effect of different enzymes (cellulase, xylanase and pectinase) on the hydrolysis of the insoluble polysaccharides in soybean meal. Cellulase, xylanase and pectinase are the major enzymes that are most responsible for the hydrolysis of the carbohydrates. The effect of each enzyme was studied by varying the ratios of these enzymes in the enzyme mixture.

Design of the Experiment

It has been found that different fermentation batches of enzyme broth will have different levels of cellulase, xylanase and pectinase activity. So, three different enzyme broths prepared from three different fermentation runs using *Trichoderma reesei* were prepared. These batches had the following enzyme levels—Batch 1: cellulase 2.66 FPU/ml, xylanase 205.9 U/ml, pectinase 8.3 U/ml, Batch 2: cellulase 2.06 FPU/ml, xylanase 66.7 U/ml, pectinase 17.2 U/ml, and Batch 3: cellulase 2.7 FPU/ml, xylanase 35.2 U/ml, pectinase 9.51 U/ml. Seven systems were prepared by mixing in different ratios of the three batches of enzyme broth such that each system had the same total enzyme activity of 50 U per g of soybean meal but different activity of each enzyme. In the control system, no enzymes were added. These eight systems are identified on Table 1, below. The soybean meal to liquid ratio (weight-to-volume) in each system was 4:1. Temperature and pH were maintained at 50° C. and 4.8, respectively, which are believed to be the optimum conditions. Experiment was performed in a 250 ml Erlenmeyer flask with working volume of 50 ml.

TABLE 1

Activity of enzyme mixtures per gram of soybean meal in different systems

| | Activity per g of soybean meal | | |
|---|---|---|---|
| | Cellulase | Xylanase | Pectinase |
| System 1 | 0.61 | 47.47 | 1.91 |
| System 2 | 0.66 | 46.73 | 2.61 |
| System 3 | 0.71 | 45.98 | 3.30 |
| System 4 | 0.81 | 44.49 | 4.70 |
| System 5 | 1.02 | 41.51 | 7.48 |
| System 6 | 1.12 | 40.02 | 8.87 |
| System 7 | 2.85 | 37.12 | 10.03 |
| Control | 0 | 0 | 0 |

Figure 5:
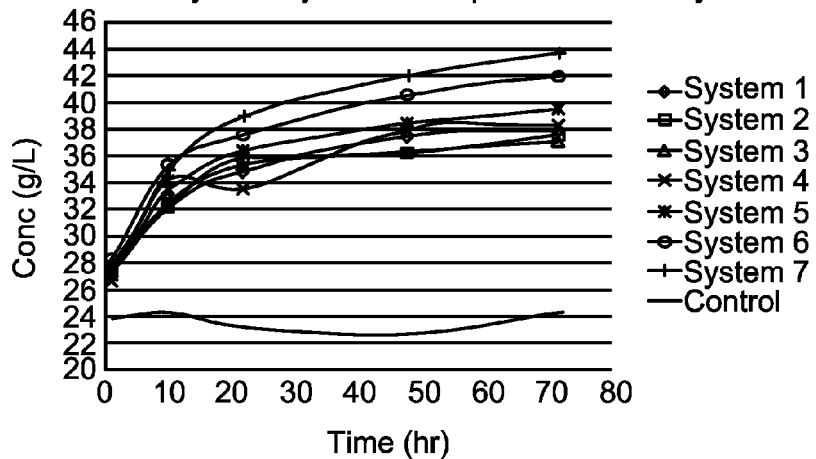
FIG. 5 is a graph showing total carbohydrate concentration in the hydrolysate measured by the phenol sulfuric acid assay according to at least one embodiment of the present invention.

Systems 1 through 7 and the control were allowed to react for approximately 72 hours. The reducing sugar concentration in the liquid (hydrolysate) for each System was measured by the standard DNS assay at 12 hours, 24 hours, 48 hours and 72 hours. The results of these DNS assays are shown in FIG. 4. The total carbohydrate concentration in the liquid for each System was measured by the phenol sulfuric acid assay at 12 hours, 24 hours, 48 hours and 72 hours. The results of these phenol sulfuric acid assays are shown in FIG. 5.

Experimental Results

From the reducing sugar analysis it was found that Systems 6 and 7 show the highest amounts of reducing sugar released after hydrolysis for three days. Reducing sugar concentration also increased with an increase in the pectinase and cellulase. Similar trend was found from total carbohydrate analysis (measures all kinds of carbohydrates including monomers, oligomers, and polymers).

Conclusion and Discussion

From the observed results, it was found that both the total carbohydrate and reducing sugar concentrations increased with increasing cellulase and pectinase but with decreasing xylanase. It can be concluded that high cellulase and pectinase activities increase the degree of hydrolysis. However, it cannot be concluded based upon these data that high xylanase concentrations have an adverse effect on the level of hydrolysis because, since the same total enzyme activity was used for each system, an increase in the cellulase and pectinase activity requires that the xylanase activity be decreased. The enzyme broths for all three fermentation batches showed far greater xylanase activity than cellulase and/or pectinase activity, and this disparity is also reflected in the systems tested. So, if the xylanase activity in all of the systems is already higher than required for hydrolysis, then the effect of xylanase on hydrolysis in these systems cannot be determined from these data. The increase in the total carbohydrate and reducing sugar concentrations may be because of the increasing cellulase and pectinase.

Example 3

Evaluation of the Effect of Pectinase on the Degree of Hydrolysis

Experimental Design

Totally, six systems were used in this study (see Table 2). All the systems except System 1 had similar total enzyme activity per gram of soybean meal. Enzymes in three of the systems came from three *T. reesei* fermentation broths, each being produced using one type of enzyme-inducing substrate, i.e., soy hull (System 1), a mixture of soy hull and soy flour (System 2), and soy flour (System 3). Commercial pectinase from Sigma Aldrich was used in Systems 4 and 5, as duplicates, to see the effect of high pectinase activity (alone) on the hydrolysis. System 6 had enzymes from a mixture of commercial pectinase and the soy hull-induced fermentation broth. Upon completion of hydrolysis, the solid protein matter was separated and collected from the liquid material by centrifugation. The liquid hydrolysate was diluted with water of 10-fold volume or was adjusted for pH (in the range of about 4.5 to about 4.8) to precipitate out the dissolved proteins. The precipitated proteins were also collected by centrifugation. For each system, the soluble total carbohydrates and reducing sugars were determined using DNS and phenyl acid assays. The total carbohydrate and reducing sugar concentrations measured were divided by the maximum carbohydrate concentration releasable from the amount of soybean meal used in each hydrolysis system. The percentages thus obtained are set forth in FIG. 6 to indicate the percent completion of carbohydrate hydrolysis in these systems. For each system, (1) the initial protein recovery (in the solid product SPC collected right after the hydrolysis experiment), (2) the protein recovery achieved by combining the initial solid product and the additional protein precipitated by adjusting the hydrolysate pH (in the range of about 4.5 to about 4.8), and (3) the protein recovery achieved by combining the initial solid product SPC and the additional protein SPI precipitated by diluting the hydrolysate with 10-fold volume of water, were also determined and are set forth in FIG. 7. Protein recovery, given as %, is calculated as the recovered amount of protein in products divided by the total amount of protein in the initial soybean meal sample used in each hydrolysis experiment. For each system, the protein content (i.e., the weight percent of protein in total solids) was also determined for (1) the initial solid product (SPC) collected right after the hydrolysis experiment, (2) the combined SPC and the SPI collected from hydrolysate diluted by 10-fold volume of water, and (3) only the SPI collected by the above water dilution method. These protein content percentages are set forth in FIG. 8.

TABLE 2

Effect of pectinase alone, enzyme mixtures from different fermentation broths, and mixture of pectinase and a fermentation broth on hydrolysis of soybean meal

| System | Liquid enzyme media | Total activity (U/g meal) |
|---|---|---|
| 1 | Soy hull-induced fermentation broth | 500 |
| 2 | Broth produced with both soy hull and soy flour as inducing substrate | 249 |
| 3 | Soy flour-induced fermentation broth | 248 |
| 4 | Commercial pectinase | 243 |
| 5 | Commercial pectinase | 247 |
| 6 | Mixture of commercial pectinase and soy hull-induced fermentation broth | 253 |

Results and Discussion

Figure 6:
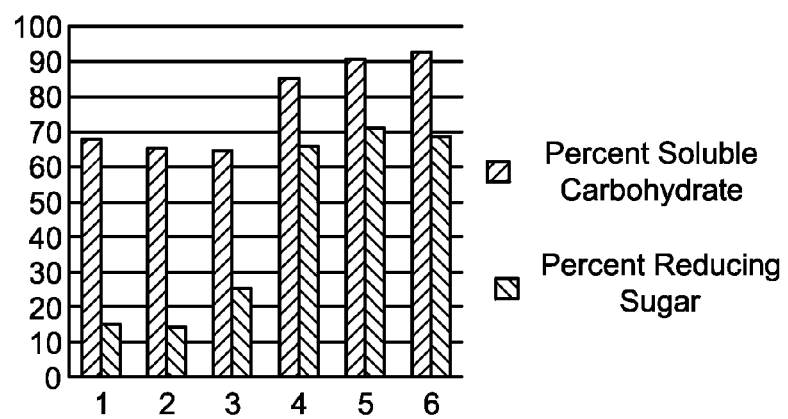
FIG. 6 is a graph showing the percent completion of carbohydrate hydrolysis achieved using different liquid enzyme media according to at least one embodiment of the present invention. The percent completion of carbohydrate hydrolysis is evaluated in two different ways: one as the percent of soybean meal carbohydrates being hydrolyzed into soluble carbohydrates in the hydrolysate, measured by the phenol sulfuric acid analysis, and the other as the percent of soybean meal carbohydrates being hydrolyzed into soluble reducing sugars in the hydrolysate, measured by the DNS analysis.
Figure 7:
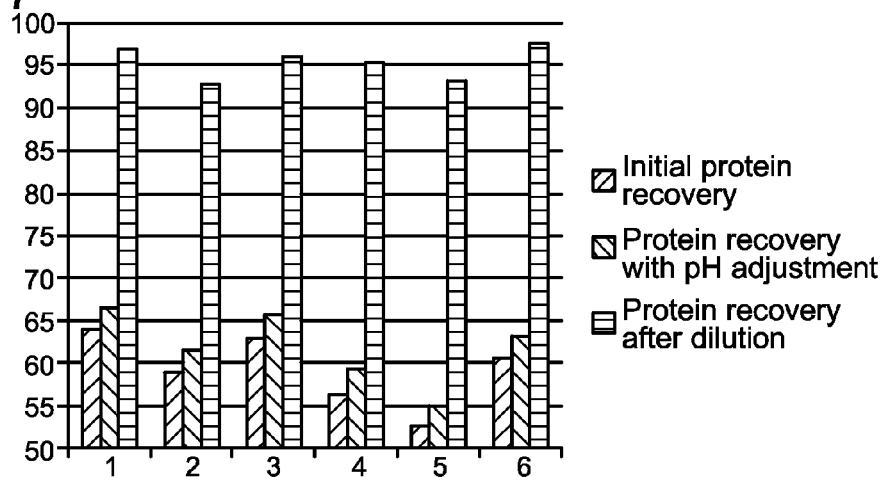
FIG. 7 is a graph showing the percent of protein recovered in solid soy products after a soybean meal sample was hydrolyzed using different liquid enzyme media according to at least one embodiment of the present invention. The percent protein recovery is shown for three methods: the first for the protein recovered in the initial product that remained as solids after the hydrolysis process, the second for the protein recovered in the solid product after the pH of hydrolysate was adjusted to 4.5 which is the isoelectric point of soy protein, and the third is the protein recovered in both the solid product after the pH adjustment and the additional solid (protein) precipitated from the hydrolysate by a dilution method.
Figure 8:
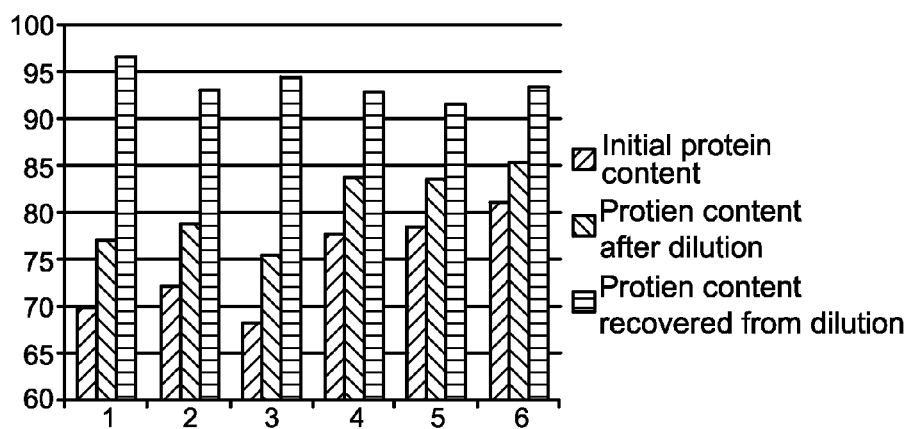
FIG. 8 is a graph showing (1) protein content in the initial solid product, (2) protein content in the combined initial solid product and the precipitated solid collected by the dilution method, and (3) protein content in the precipitated solid collected by the dilution method, for a study of soybean meal hydrolysis using different liquid enzyme media according to at least one embodiment of the present invention.

Hydrolysis results by the commercial pectinase were compared with the results by *T. reesei* broths. The *T. reesei* strain (Rut-C30 NRRL 11460) was obtained through USDA's ARS culture collection (NRRL). It was found that the commercial pectinase gave a higher degree of soybean carbohydrate hydrolysis (almost 80-90% of the carbohydrates were released into the liquid hydrolysate) than the 3 *T. reesei* broths did (60-65% carbohydrates released) (FIG. 6). In addition, the differences between the % release as total soluble carbohydrates and the % release as reducing sugars were smaller in the systems hydrolyzed with commercial pectinase than in the systems with *T. reesei* broths (FIG. 6). The smaller differences indicated that the high pectinase activity alone could break down the soluble oligosaccharides into monosaccharides more completely. Further, protein content in the initial solid product SPC was found to be higher in the systems with the commercial pectinase (about 80%) than in the systems with only the *T. reesei* fermentation broths (about 70-73%) (FIG. 8). Protein recovery in the initial solid product SPC was found to be about 60-65% in the systems with the *T. reesei* fermentation broths but was only 52-60% in the systems with commercial pectinase (FIG. 7). The observation indicated that more protein would become soluble in the hydrolysate as more oligosaccharides and polysaccharides were hydrolyzed, as achieved by the commercial pectinase. Significant amount of protein was found in the hydrolysate in all of the systems. Protein in the hydrolysate can be recovered by dilution with a large amount of water, which helps to increase the protein recovery to more than 90%. But this dilution method makes the hydrolysate low in saccharide concentration, less useful as a substrate source for production of arabitol or other fermentation products.

Example 4

Comparison of *T. reesei* Rut-C30 and *A. niger* NRRL 341 Enzyme Productivity

Procedure

From the previous study (See Example 1) of *Trichoderma reesei* Rut-C30 NRRL 11460 fermentation with different carbon sources and nitrogen sources, the soy hulls as carbon source can induce the cellulase and xylanase production, especially at high pH (about 6.0). At a lower pH (about 4) the soy hulls are good for pectinase production. But from the hydrolysis results, the enzyme broth from *T. reesei* gave lower protein contents after soy flour hydrolysis than did the commercial pectinase from an *A. niger* culture. The commercial pectinase was obtained from Sigma Aldrich (Saint Louis, Mo.). It has been found that the composition of enzyme broth generated by the *T. reesei* fungus is not the best composition for hydrolysis of soy flour.

Accordingly, a study of the enzyme activity of *A. niger* NRRL 341 was carried out. First, a shake-flask study of *A. niger* in different combinations of carbon sources and nitrogen sources (labeled as Systems 1-4 in Table 3) with an initial pH 5.0 was carried out. Then another shake-flask study was carried out to determine whether *A. niger* NRRL 341 has the potential to produce higher enzyme activities than *T. reesei* Rut-C30 NRRL 11460 (labeled as Systems 1-4 in Table 4).

Flasks were inoculated with 10 vol % of an aqueous suspension of *A. niger* or *T. reesei* spores and grown for 5 days, with an initial medium pH of 5. Daily samples were removed and assayed for pH and enzyme activity. The enzyme activity measurements were made with the supernatants collected by centrifugation, after the cells and other solids in the broth samples were removed. Cellulase was assayed using a standard FPU test using filter paper as substrate, reacting it with the collected supernatant at 50 C for 1 hour, and testing the releasing reducing sugars. Xylanase was assayed using xylan as substrate, reacting it with the supernatant sample at 50° C. for 5 min, and testing the releasing sugar. Pectinase was assayed using polygalacturonic acid as substrate, reacting it with the supernatant at 50 C for 30 min, and testing the releasing sugar.

Results

The results of the *A. niger* shake-flask study are summarized in Table 3, below.

TABLE 3

Enzyme activities of *A. niger* flask shake study

| Fermentation System | Nitrogen Source | Carbon source | Cellulase (U/mL) | Xylanase (U/mL) | Pectinase (U/mL) |
|---|---|---|---|---|---|
| System1 | $(NH_4)_2SO_4$ - 1.4 g/L | Sucrose - 10 g/L | 0.09 ± 0.01 | 0.28 ± 0.27 | 0.42 ± 0.10 |

TABLE 3-continued

Enzyme activities of *A. niger* flask shake study

| Fermentation System | Nitrogen Source | Carbon source | Cellulase (U/mL) | Xylanase (U/mL) | Pectinase (U/mL) |
|---|---|---|---|---|---|
| System2 | Urea - 0.3 g/L Proteose peptone -1 g/L soyflour - 7.04 g/L | Sucrose - 7.75 g/L | 0.13 ± 0.01 | 6.8 ± 1.1 | 0.37 ± 0.08 |
| System3 | (NH₄)₂SO₄ - 1.4 g/L Urea - 0.3 g/L Proteose peptone -1 g/L | Soyhulls - 20 g/L | 0.44 ± 0.03 | 44.7 ± 1.6 | 5.04 ± 0.20 |
| System4 | Soyflour - 7.04 g/L | Soyhulls - 15.5 g/L | 0.37 ± 0.01 | 39.3 ± 3.1 | 1.27 ± 0.20 |

Figure 9:
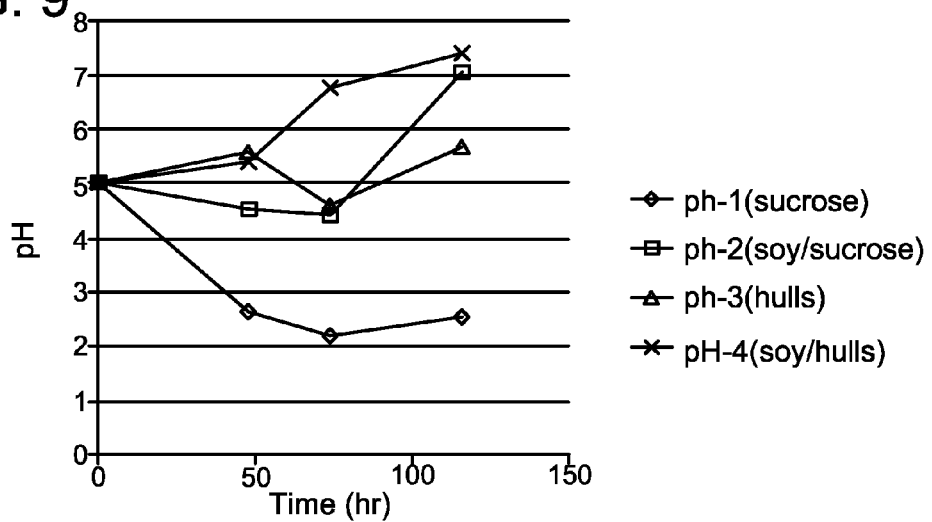
FIG. 9 is a graph showing the pH change over time for a study with *A. niger* culture in shake flasks involving four different carbon substrates prepared according to at least one embodiment of the present invention.

The pH of Systems 1 through 4 was checked at regular intervals and the data collected. The pH values for each System are set forth in FIG. 9. These 4 systems gave significantly different pH change trends, indicating that the C and N sources have significant effects on the cell growth, cell metabolism, and substrate consumption.

Figure 10:
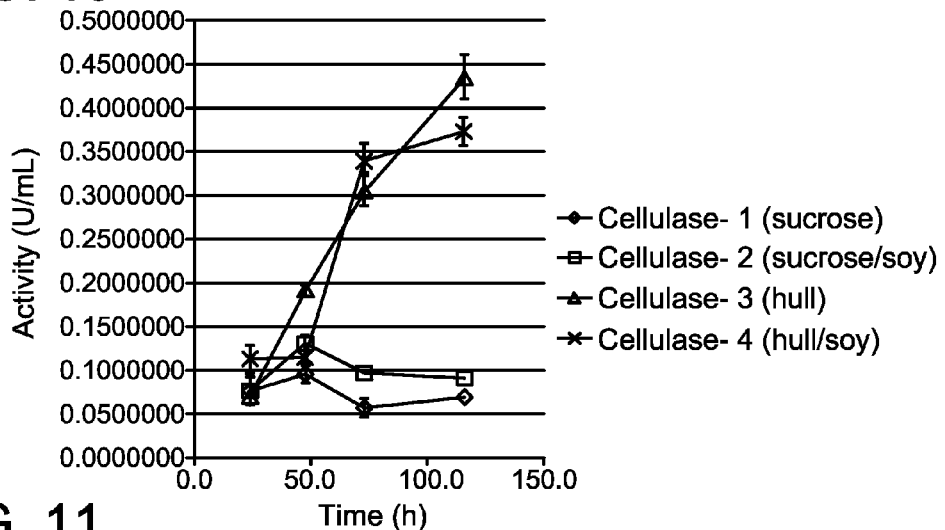
FIG. 10 is a graph showing cellulase production during an *A. niger* study performed in shake flasks using four different carbon substrates prepared according to at least one embodiment of the present invention.

The results of the assays of cellulase activity done for Systems 1 through 4 are shown in FIG. 10. As can be seen in FIG. 10, the cellulase production trends for System 3 and System 4 continuously increased during the observed time, whereas the cellulase production trends for System 1 and System 2 decreased after the first 48 hrs.

Figure 11:
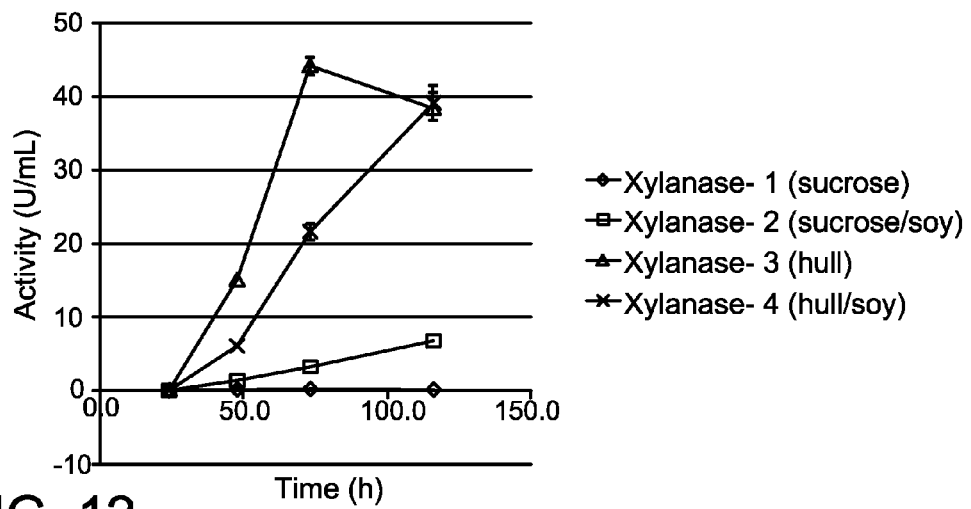
FIG. 11 is a graph showing xylanase production during an *A. niger* study performed in shake flasks using four different carbon substrates prepared according to at least one embodiment of the present invention.

The results of the assays of xylanase activity done for Systems 1 through 4 are shown in FIG. 11. As can be seen in FIG. 11, Systems 3 and 4 gave significantly higher xylanase production rates than System 1 and/or System 2. The xylanase activity for System 4 was comparable to that of System 3, until the same last observed point.

Figure 12:
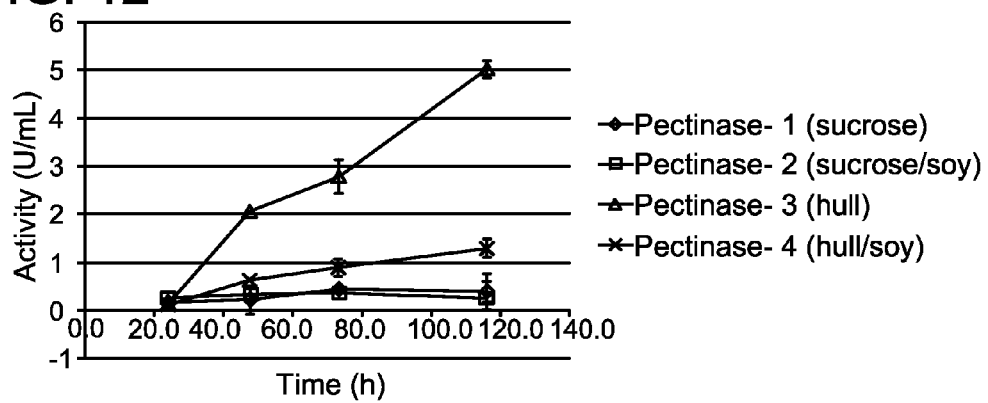
FIG. 12 is a graph showing pectinase production during an *A. niger* study performed in shake flasks using four different carbon substrates prepared according to at least one embodiment of the present invention.

The results of the assays of pectinase activity done for Systems 1 through 4 are shown in FIG. 12. As can be seen from FIG. 12, the pectinase production behavior of System 3 was much better than that of the other 3 systems. Systems 1 and 2 provided a very low level of production. While not as low as Systems 1 and 2, the pectinase activity for System 4 was also much lower than that of System 3.

From these four different systems, Systems 3 and 4 provided better enzyme production than did Systems 1 and 2. Therefore, the medium compositions of Systems 3 and 4 were selected as the study medium for the subsequent comparison study with *T. reesei*.

TABLE 4

Enzyme activities for *T. reesei* and *A. niger* compared in a shake-flask study

| Fermentation System | Nitrogen Source | Carbon source | Cellulase (U/mL) | Xylanase (U/mL) | Pectinase (U/mL) |
|---|---|---|---|---|---|
| System1 (*T. reesei*) | (NH₄)₂SO₄ - 1.4 g/L Urea - 0.3 g/L Proteose peptone -1 g/L | Soyhulls - 20 g/L | 0.85 ± 0.05 | 82.3 ± 5.3 | 0.24 ± 0.15 |
| System2 (*T. reesei*) | soy flour - 7.04 g/L | Soyhulls - 17.18 g/L | 0.97 ± 0.01 | 123.5 ± 5.3 | 0.45 ± 0.05 |
| System3 (*A. niger*) | (NH₄)₂SO₄ - 1.4 g/L Urea - 0.3 g/L Proteose peptone -1 g/L | Soy hulls - 20 g/L | 0.50 ± 0.01 | 79.5 ± 2.6 | 2.5 ± 0.3 |
| System4 (*A. niger*) | soy flour - 7.04 g/L | Soyhulls - 17.18 g/L | 0.31 ± 0.00 | 26.2 ± 1.3 | 0.44 ± 0.05 |

Figure 13:
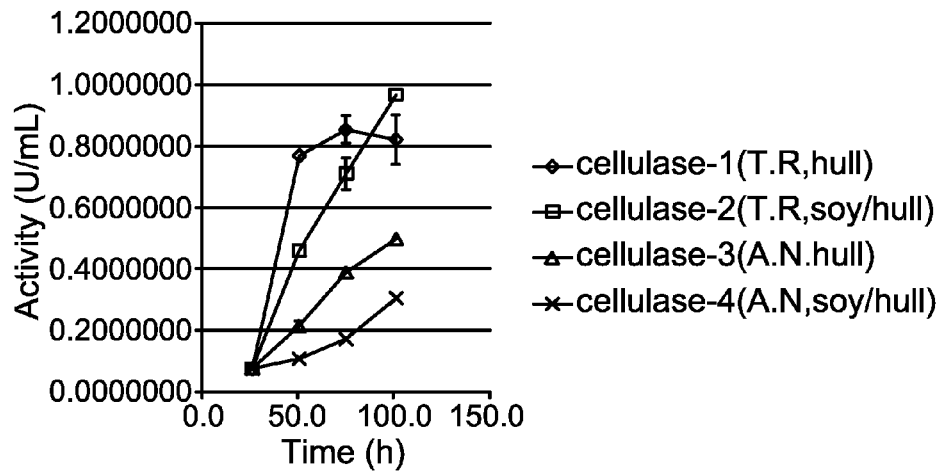
FIG. 13 is a graph comparing cellulase production by a *T. reesei* strain and an *A. niger* strain using two different carbon substrates prepared according to at least one embodiment of the present invention.
Figure 14:
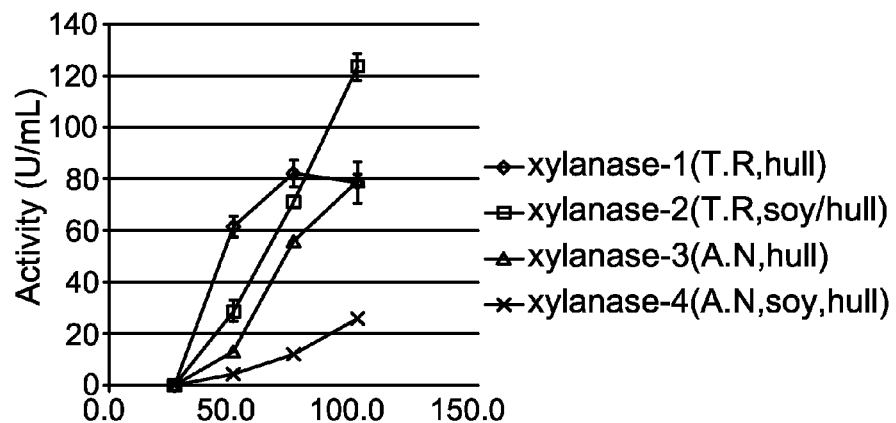
FIG. 14 is a graph comparing xylanase production by a *T. reesei* strain and an *A. niger* strain using two different carbon substrates prepared according to at least one embodiment of the present invention.
Figure 15:
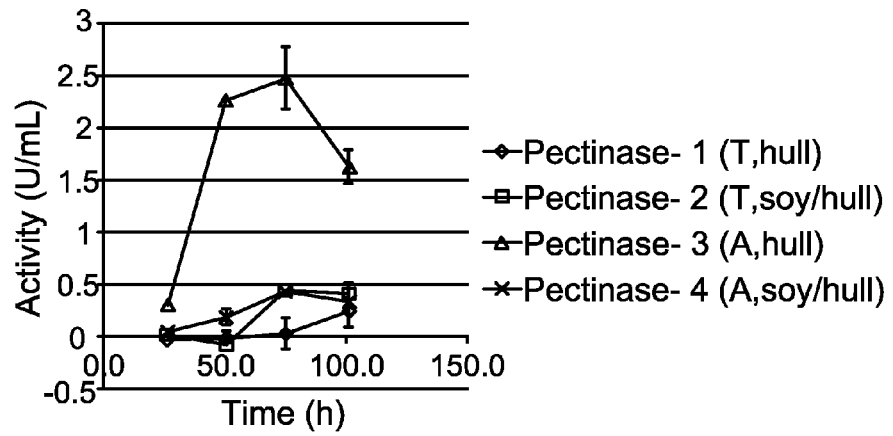
FIG. 15 is a graph comparing pectinase production by a *T. reesei* strain and an *A. niger* strain using two different carbon substrates prepared according to at least one embodiment of the present invention.

As can be seen in Table 4, above and in FIGS. 13-15, Systems 1 and 2 gave higher cellulase and xylanase production than did either System 3 or System 4. However, System 3 gave much higher pectinase production than did the other 3 systems.

As can be seen in Table 4, above and in FIG. 13, Systems 1 and 2 were better than Systems 3 and 4 in cellulase production. For *T. reesei*, System 2 was better than System 1, from which it may be concluded that soy flour induced *T. reesei* to produce more cellulase than did the nitrogen source of System 1 (1.4 g/L of (NH₄)₂SO₄, 0.3 g/L of urea, and 1 g/L of Proteose peptone). As can also be seen in Table 4, above and in FIG. 14, Systems 1 and 2 were better than Systems 3 and 4 in xylanase production. For *T. reesei*, System 2 was better than System 1, from which it may be concluded that soy flour induced *T. reesei* to produce more xylanase than did the nitrogen source of System 1 (1.4 g/L of (NH₄)₂SO₄, 0.3 g/L of urea, and 1 g/L of Proteose peptone). As can be further seen in Table 4, above and in FIG. 15, System 3 gave the higher pectinase production than did the other 3 systems. The pectinase production was comparable for the other 3 systems.

Conclusion

From the *A. niger* shake-flask study (Table 3), it is clear that soy hulls can induce cellulase and xylanase production. Further it may be concluded the systems with soy hulls as substrate have higher cellulase and xylanase production than the systems with sucrose or a sucrose/soy flour mixture. And the soy hulls system (System 3 of the *A. niger* study) has the highest pectinase production. Based on these findings, soy hulls medium and soy hull with soy flour medium were selected as the media for the *T. reesei* and *A. niger* comparison shake-flask study.

From the two strains comparison results, it can be concluded that *T. reesei* Rut-C30 NRRL 11460 produces higher levels of cellulase activity than does *A. niger* NRRL 341 given the same medium. It may also be concluded that although *T. reesei* and *A. niger* show comparable xylanase production, *A. niger* has the potential to produce more pectinase than does *T. reesei*.

Example 5

Evaluation of the Fermentation Conditions for *A. niger* 341

Procedure

The pectinase is very important in degrading the soy flour as 10% of soy flour carbohydrates are pectins. Although *T. reesei* is a good cellulase and xylanase producer, it is not a good pectinase producer. On the other hand, most of *A. niger* strains studied have been found to give good pectinase production. (See Example 7). *A. niger* strain number (NRRL) 341 was selected based upon the description provided by from Northern Regional Research Laboratory (NRRL) (through the United States Department of Agriculture Agricultural Research Service (ARS)), which identifies *A. niger* 341 as a pectinase producer.

Two 1.5 L fermentations were carried out using 20 g/L soybean hulls as the carbon source. And one 1.5 L fermentation was carried out using 40 g/L soybean hulls powder as the carbon source. One more 1.5 L fermentation was carried out using 20 g/L soy hulls powder as the carbon source and doubled nitrogen source. The fermentation batches were labeled FerA1, FerA2, FerA3 and FerA4 and are described on Table 5, below. In addition, FerA1 was operated at initial pH of 4.5, with no subsequent controls. FerA2 was operated at an initial pH or 4.5, which was kept substantially constant for the duration of the experiment. FerA3 and FerA4 were operated at an initial pH of 5.0, which was kept substantially constant for the duration of the experiment.

Daily samples were removed and assayed for enzyme activities. The cellulase test used followed the standard Filter-Paper Unit (FPU) test method. (See, Ghose T. *Measurement of cellulase activities*. Pure Appl Chem 1987; 59:257, the disclosure of which is incorporated herein by reference in its entirety).

The standard xylanase and pectinase test methods used were modified follows.

Xylanase Activity Measurement (1) Add 0.9 mL suspended xylan (shake to mix first) to the blank tubes and seal with parafilm.
(2) Add 0.1 mL enzyme solution (supernatant of the broth; appropriately diluted) to sample test tube.
(3) Add 0.9 mL suspended xylan (shaking to mix) to the sample test tubes and seal with parafilm.
(4) Place in water bath at 50° C. for 5 minutes.
(5) Terminate reaction with 3 mL DNS solution.
(6) Add 0.1 mL enzyme solution to the blanks.
(7) Use DNS method to determine the concentration of xylose. (Measure absorbance at 540 nm).

To make suspended xylan:
(1) Measure 1 g xylan
(2) Add to beaker with 80 mL 0.05M (pH=5.3) sodium citrate buffer
(3) Heat and stir until steam just begins to condense above liquid and suspension appears uniform
(4) Turn off heat, cool, cover, and stir overnight
(5) Add citrate buffer to bring volume to 100 mL
(6) Store for 2 days at 4° C. or for longer periods at −20° C. (shake after freezing)

Enzyme activity is reported in units per milliliter (U/mL). 1 U=1 µmol product released per minute. The effective range of this test is 0.5 to 2.0 U/mL. The test accuracy diminishes beyond that range.

Pectinase Activity Measurement (1) Add 0.9 mL suspended polygalacturonic acid (shake to mix first) to the blank tubes and seal with parafilm.
(2) Add 0.1 mL enzyme solution (supernatant of the broth; appropriately diluted) to sample test tube.
(3) Add 0.9 mL suspended polygalacturonic acid (shaking to mix) to the sample test tubes and seal with parafilm.
(4) Place in water bath at 50° C. for 30 minutes.
(5) Terminate reaction with 3 mL DNS solution.
(6) Add 0.1 mL enzyme solution to the blanks.
(7) Use DNS method to determine the concentration of galacturonic acid. (Measure absorbance at 540 nm).

To make suspended polygalacturonic acid:
(1) Add to beaker with 100 mL 0.1M (pH=4.8) sodium citrate buffer
(2) Measure 0.5 g polygalacturonic acid and add to beaker
(3) Adjust the final pH to 4.8
(4) Make fresh substrate in every test Enzyme activity is reported in units per milliliter (U/mL). 1 U=1 µmol product released per minute. The effective range of this test is 0.3 to 0.7 U/mL. The test accuracy diminishes beyond that range.

Results

Figure 16:
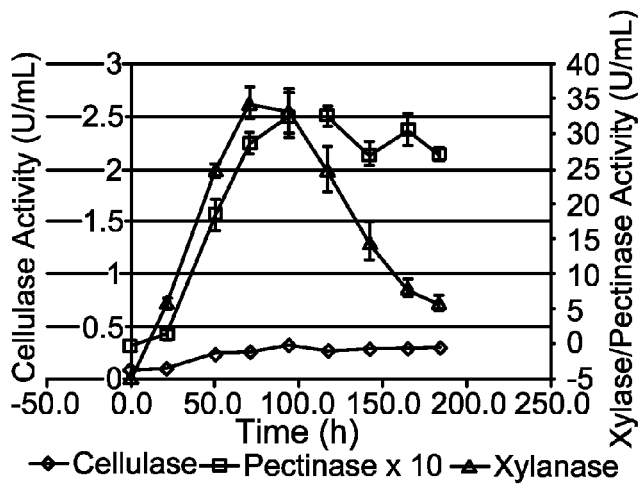
FIG. 16 is a graph showing enzyme production by *A. niger* NRRL 341 for the fermentation batch labeled as FerA1 prepared according to at least one embodiment of the present invention.

The results of the enzyme activity assays described above are shown in Table 5 and are shown in FIG. 16.

TABLE 5

The enzyme activity in various fermentation systems

| Fermentation System | Nitrogen Source | Carbon source | Cellulase (U/mL) | Xylanase (U/mL) | Pectinase (U/mL) |
|---|---|---|---|---|---|
| FerA1 (pH 4.5-no control) | $(NH_4)_2SO_4$ - 1.4 g/L Urea - 0.3 g/L Proteose peptone -1 g/L | Soyhulls - 20 g/L | 0.32 ± 0.01 | 32.5 ± 1.5 | 2.6 ± 0.1 |
| FerA2 (pH 4.5) | $(NH_4)_2SO_4$ - 1.4 g/L Urea - 0.3 g/L Proteose peptone -1 g/L | Soyhulls - 20 g/L | 0.32 ± 0.00 | 50.95 ± 1.46 | 2.5 ± 0.1 |
| FerA3 (pH 5.0) | $(NH_4)_2SO_4$ - 1.4 g/L Urea - 0.3 g/L Proteose peptone -1 g/L | Soyhulls - 40 g/L | 0.64 ± 0.03 | 142.4 ± 1.6 | 4.15 ± 0.15 |
| FerA4 (pH 5.0) | $(NH_4)_2SO_4$ - 2.8 g/L Urea - 0.6 g/L Proteose peptone -2 g/L | Soyhulls - 20 g/L | 0.61 ± 0.03 | 65.1 ± 1.7 | 2.6 ± 0.1 |

Conclusion

Figure 17:
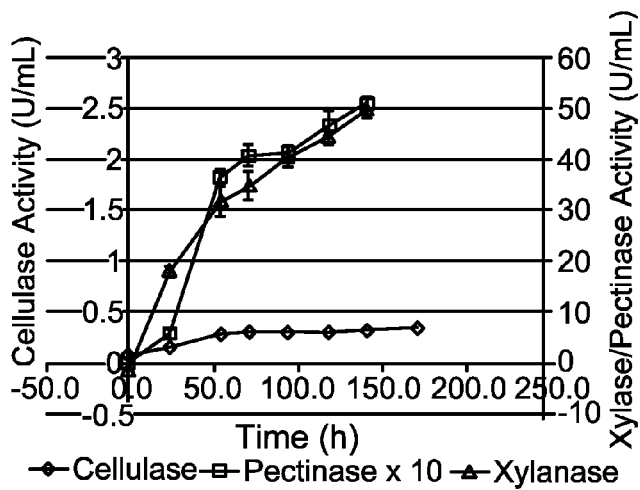
FIG. 17 is a graph showing enzyme production by *A. niger* NRRL 341 for the fermentation batch labeled as FerA2 prepared according to at least one embodiment of the present invention.
Figure 18:
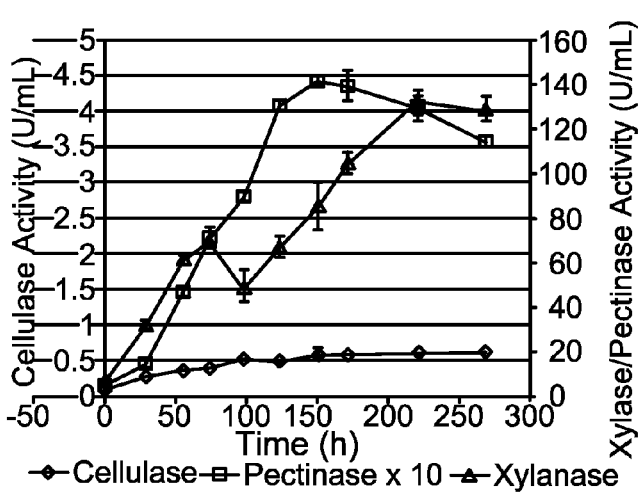
FIG. 18 is a graph showing enzyme production by *A. niger* NRRL 341 for the fermentation batch labeled as FerA3 prepared according to at least one embodiment of the present invention.
Figure 19:
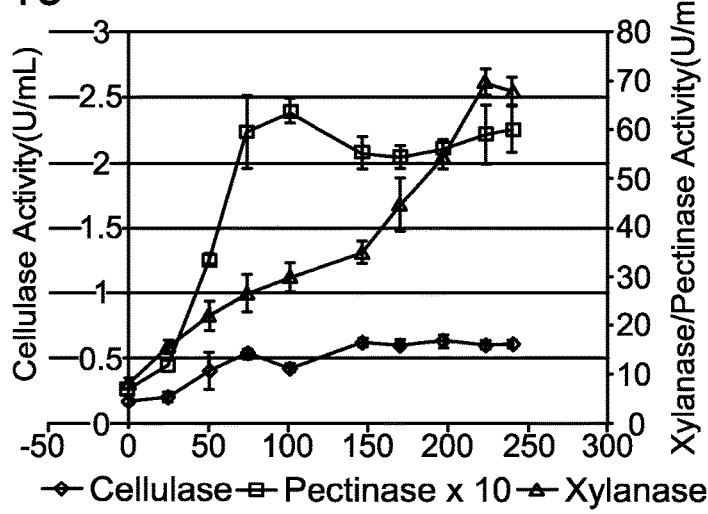
FIG. 19 is a graph showing enzyme production by *A. niger* NRRL 341 for the fermentation batch labeled as FerA4 prepared according to at least one embodiment of the present invention.

As can be seen from these results, system FerA1 gave a poorer enzyme production (See FIG. 16) than did the other 3 systems (FerA2 (FIG. 17), FerA3 (FIG. 18) and FerA4 (FIG. 19)). It is believed that are at least two possible reasons for this. The first it is believed that the lack of control over the pH lead to the lower enzyme production. Second, the soy hulls used for these experiments were unground. Comparing FerA2 to FerA4, it can be seen that a doubling of the carbon source doubled production of all three enzymes, and a doubling nitrogen source doubled only cellulase production. It is apparent that this *A. niger* specie used the carbon source and nitrogen source faster than *T. reesei*, but gave lower enzyme production than *T. reesei* previous fermentation runs.

Example 6

Screening of 6 Strains of *Aspergillus Niger* for their Ability to Utilize Soy Molasses Sugars as their Carbon Source

Experimental Design

Soy molasses is a low-cost feedstock obtained as a co-product stream in soybean oil processing and is cheaper than glucose as a substrate. However, use of the sugar composition of soy molasses as an effective carbon source due is challenging due to the presence of oligosaccharides such as raffinose, stachyose and verbascose (See Qureshi, Lolas et al. 2001, *"Soy molasses as fermentation substrate for production of butanol using Clostridium beijerinckii BA101"*—*Journal of industrial Microbiology and Biotechnology* 26(5): 290-295, the disclosure of which is incorporated herein by reference in its entirety) which introduce difficulties in their consumption mainly due to the lack of the necessary enzymes to break them down to small sugars. The ability of the 6 *Aspergillus* strains identified to grow with these oligosaccharides as the carbon source was evaluated.

Table 6, below, shows the sugar composition in soy molasses, where sucrose is the highest sugar concentration followed by stachyose and raffinose. *Aspergillus* (NRRL) strains numbers 2053, 566, 363, 341, 328 and 334 were tested for their ability to use oligosaccharides raffinose and stachyose as carbon source for growth. This screening study also evaluates the use of soy molasses as the carbon source for selected fungal strains for the production of desired enzymes.

TABLE 6

Concentrations of different sugars in the soy molasses.

| Component | Molasses Concentration (wt %) |
|---|---|
| Sugar Total | 20.65 |
| Arabinose | — |
| Fructose | 0.7 |
| Galactose | — |
| Glucose | 0.3 |
| Raffinose | 1.4 |
| Rhamnose | — |
| Stachyose | 6.9 |
| Sucrose | 11.3 |
| Xylose | — |

Materials and Methods

The enzyme strains that were used for the screening experiments describe herein were *Aspergillus aculeatus* (NRRL) strain number 2053 and *Aspergillus niger* (NRRL) strain numbers 566, 363, 341, 328 and 334. These fungi are commercially available and were obtained from ARS. Table 7 shows the medium compositions that were used for the screening process. The Raffinose systems were evaluated in 125 ml Erlenmeyer flasks each having a culture volume of 25 ml and the Stachyose systems were evaluated in 10 ml test tubes, each having a 2 ml culture volume. The flasks and test tubes were covered with cheesecloth with cotton placed inside. These systems were agitated in an orbital shaker at 200 rpm and at 30° C. temperature. Spores of 6 different *Aspergillus* strains were inoculated with sterilized loop twice in their respective flasks and test tubes.

TABLE 7

Medium composition used for screening study with soy molasses used as the carbon source.

| | g/L |
|---|---|
| Ammonium sulfate | 1.4 |
| Urea | 0.3 |
| Protease peptone | 1.0 |

TABLE 7-continued

Medium composition used for screening study with soy molasses used as the carbon source.

| | g/L |
|---|---|
| $K_2HPO_4$ | 0.028 |
| Raffinose/Stachyose | 10 |

These systems were kept on the shaker for 5 days. Samples were taken from these systems at the end of 5th day and were analyzed for cell and sugar concentrations.

1. Cell Concentration

Figure 20:
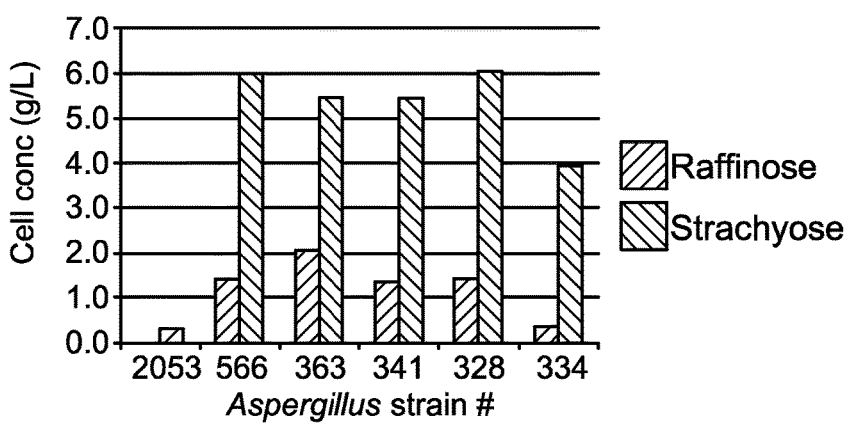
FIG. 20 is a graph showing cell concentration in g/L attained after 6 *Aspergillus* strains had been grown for 5 days in media containing either raffinose or stachyose as the sole carbon source and prepared according to at least one embodiment of the present invention. The ability to grow is taken to indicate the strain's production of enzyme(s) capable of hydrolyzing raffinose or stachyose to consumable saccharide(s).

Cell concentrations were determined by measuring the dry weights of the sample. The dry weights were determined by first centrifuging a 25 ml sample in case of raffinose systems and a 2 ml sample in the case of the stachyose systems at 9000 rpm for 10 min to separate the solids from supernatant which was saved for further analysis. After separation from supernatant, the cell pellets were dispersed in deionized (DI) water and centrifuged again under same conditions. The supernatant in this step was discarded. The cell pellet was again dispersed in DI water and the transferred to an aluminum pan of known weight. These pans were placed in the oven at 100° C. for 24 h. The pan weight was measured after 24 h and the difference in the weight from the initial was used to calculate the cell concentration. The results of the cell concentration assays for the raffinose and stachyose systems are shown in FIG. 20.

2. Sugar Analysis

Raffinose and stachyose were measured using a standard phenol sulfuric acid test as follows. Glucose was used as the standard for the calibration in this test over a range of 0.02 to 0.1 g/L. Supernatant samples from each of the systems shown on Table 8 (below) were diluted so that the concentrations of raffinose and stachyose were within the calibration range set forth above. 1 ml of 5% phenol was added to 1 ml of each sample in 10 ml test tubes, followed by 5 ml of concentrated sulfuric acid. The test tubes were allowed to cool for 5 min and were then mixed on a vortex mixer before being set aside for 10 min. After 10 min, the absorbance of the samples and the standards was read at 490 nm in UV-vis spectrophotometer. The concentrations of raffinose and stachyose were calculated from the calibration developed using the glucose standard.

Results

Cell concentrations was measured for the 6 *Aspergillus* strains both in systems where raffinose was only carbon source and in systems where stachyose was the only carbon source. These cell concentrations are shown in FIG. 20. *Aspergillus aculeatus* 2053 was the only strain which had poor/no growth in both the raffinose and stachyose systems. For *Aspergillus niger* strain numbers 566, 363, 341 and 328, the cell growth was significant in both the raffinose and stachyose systems, but the final cell concentrations reached after 5 days for the raffinose and stachyose systems was significantly for the raffinose and stachyose systems, with the cell growth being better in the stachyose systems. (See FIG. 20). The ability of these strains to utilize stachyose better for cell growth than raffinose was also confirmed by the sugar analysis showing the consumption of the raffinose and stachyose at the end of the 5th day. This consumption was recorded and is shown in Table 8. Stachyose was better consumed in these strains than raffinose and hence the cell concentration was better in the stachyose systems.

TABLE 8

Residual raffinose and stachyose

| Aspergillus Strain # | Raffinose, g/L | Stachyose, g/L |
|---|---|---|
| 2053 | 0 | 0.9 |
| 566 | 3.2 | 9.4 |
| 363 | 3.9 | 9.7 |
| 341 | 5.7 | 7.0 |
| 328 | 2.4 | 7.4 |
| 334 | 1.6 | 7.1 |

Discussion

Raffinose is the oligosaccharide with galactose, glucose and fructose whereas stachyose has an additional galactose unit. For these oligosaccharides to be consumed as the carbon source, these sugars need to be cleaved in to monosaccharides. This may be done by the enzyme α-galactosidase which cleaves the bond between each galactose unit and by invertase for breaking sucrose into glucose and fructose units. So, it is the same enzyme α-galactosidase that was required for the stachyose and raffinose sugar and should result in the same cell growth in both the systems unless the activity of these enzymes is different. It could be hypothesized that the enzyme activity of α-galactosidase with stachyose as carbon source could be higher than raffinose as carbon source, which lead to the differences in the cell growth. According to literature survey on these enzyme activities with different carbon sources, different sugars induce differences in the activities of the enzymes. (See, M. S. Garro, G. F. de Valdez, G. Oliver and G. S. de Giori. (1996) Current microbiology 33, 302-305, the disclosure of which is hereby incorporated by reference in its entirety). These studies with this bacteria reported that when stachyose, melibiose, raffinose and glucose were used as carbon sources individually, α-galactosidase activity was high in case of stachyose as the only carbon source followed by melibiose and raffinose.

Where stachyose and raffinose are considered together as in case of soy molasses, the enzyme activity would be high, helping the consumption of both raffinose and stachyose. Hence, it can be concluded that Aspergillus strains 566, 363, 341 and 328 could be used for production of enzymes with soy molasses as the carbon source.

Example 7

A. niger Strain Screening

Procedure

From the hydrolysis results described above, it can be concluded that A. niger has the potential to produce the right enzymes to break down more carbohydrates than T. reesei. Because there are many different A. niger strains that could be suitable, screening experiments were conducted to identify the optimum A. niger strains. Thirteen A. niger (NRRL) strains available from ALS, namely A. niger NRRL strain numbers 322, 325, 328, 334, 341, 348, 363, 566, 599, 2270, 13201, 13219, 62517, were selected for the study. Further, in order to reach a more complete conclusion, T. reesei and A. aculeatus (NRRL) strain number 2053 were also listed in the comparison.

First, the fungi were activated by potato dextrose liquid culture. Then these strains were cultured in potato dextrose agar for 72 hours. The spores were washed by sterilized DI water (with Tween80) and then inoculated in equal amounts to the flasks having soy hulls as a medium. Daily samples were taken to analyze the enzyme activities and pH change. After 72 hours, all broth was collected and used for hydrolysis tests with soy flour. Reducing sugar and total sugar concentrations were measured and analyzed during hydrolysis.

The strains showing the highest enzyme efficiency, as measured by the enzyme production and the concentration of releasing sugars those enzymes generate in hydrolysis, will be considered good strains for this process.

Results

TABLE 9

Enzyme activities of A. niger flask study

| NO. | Fungi/Strain | Nitrogen Source | Carbon source | Cellulase (U/mL) | Xylanase (U/mL) | Pectinase (U/mL) |
|---|---|---|---|---|---|---|
| 1 | A. niger 322 | $(NH_4)_2SO_4$ - 1.4 g/L Urea - 0.3 g/L Proteose peptone - 1 g/L | Soyhulls - 20 g/L | 0.31 ± 0.01 | 101.7 ± 1.5 | 15.6 ± 0.3 |
| 2 | A. niger 325 | Same | Same | 0.16 ± 0.01 | 12.5 ± 0.6 | 5.6 ± 0.0 |
| 3 | A. niger 328 | Same | Same | 0.24 ± 0.00 | 56.2 ± 5.0 | 7.5 ± 0.4 |
| 4 | A. niger 334 | Same | Same | 0.26 ± 0.01 | 87.7 ± 3.0 | 7.8 ± 0.5 |
| 5 | A. niger 341 | Same | Same | 0.37 ± 0.04 | 77.6 ± 2.7 | 2.4 ± 0.2 |
| 6 | A. niger 348 | Same | Same | 0.31 ± 0.04 | 129.9 ± 9.6 | 10.7 ± 0.4 |
| 7 | A. niger 363 | Same | Same | 0.26 ± 0.03 | 63.4 ± 1.9 | 10.4 ± 0.1 |
| 8 | A. niger 566 | Same | Same | 0.26 ± 0.01 | 52.5 ± 12.1 | 8.5 ± 0.6 |
| 9 | A. niger 599 | Same | Same | 0.19 ± 0.00 | 39.1 ± 6.5 | 7.1 ± 0.1 |
| 10 | A. niger 2270 | Same | Same | 0.26 ± 0.01 | 80.6 ± 5.3 | 14.8 ± 0.5 |
| 11 | A. niger 13201 | Same | Same | 0.41 ± 0.00 | 83.9 ± 1.0 | 13.1 ± 0.1 |
| 12 | A. niger 13219 | Same | Same | 0.20 ± 0.00 | 49.5 ± 4.5 | 14.8 ± 0.6 |
| 13 | A. niger 62517 | Same | Same | 0.29 ± 0.02 | 94.6 ± 22.4 | 5.1 ± 0.1 |
| 14 | A. aculeatus 2053 | Same | Same | 0.28 ± 0.04 | 14.5 ± 3.6 | 9.4 ± 0.4 |
| 15 | T. reesei | Same | Same | 0.70 ± 0.10 | 109.3 ± 19.8 | 3.7 ± 0.2 |

From the enzyme production results for cellulase production shown in Table 9, the enzyme activity of *A. niger* strain numbers 322, 341, 348, 13201 and *T. reseei* are all higher than 0.4 U/mL. From the enzyme production results for xylanase shown in Table 9, the enzyme activities of *A. niger* strain numbers 322 and 348, as well as *T. reesei*, are higher than 100 U/mL. From the enzyme production results for pectinase shown in Table 9, the enzyme activities of *A. niger* strain numbers 322, 348, 363, 2270, 13201, 13219 are higher than 10 U/mL.

Figure 21:
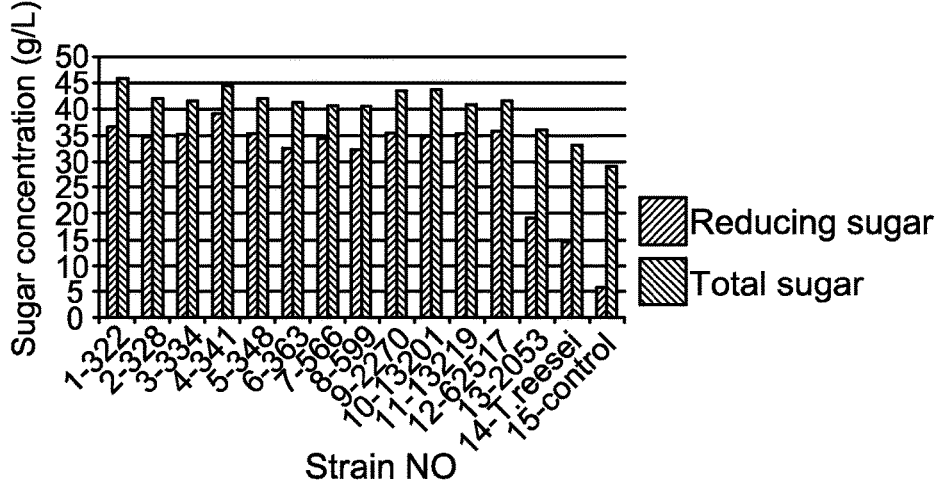
FIG. 21 is a graph showing sugar releasing results from hydrolysis by using 8-fold diluted enzyme-containing media produced from 14 fungal strains, as compared to the sugar releasing results in the enzyme-free control system (No. 15).

The results of the hydrolysis assays are set forth on Table 10 and shown in FIG. 21.

TABLE 10

Releasing sugars' concentration from hydrolysis

| No. | Fungus/Strain | Reducing sugars (g/L) | Total sugars (g/L) |
| --- | --- | --- | --- |
| 1 | A. niger 322 | 37.37 | 45.86 |
| 2 | A. niger 328 | 34.72 | 43.11 |
| 3 | A. niger 334 | 35.32 | 42.18 |
| 4 | A. niger 341 | 38.77 | 44.33 |
| 5 | A. niger 348 | 35.38 | 42.16 |
| 6 | A. niger 363 | 33.17 | 41.30 |
| 7 | A. niger 566 | 34.34 | 41.05 |
| 8 | A. niger 599 | 32.87 | 40.89 |
| 9 | A. niger 2270 | 35.43 | 43.17 |
| 10 | A. niger 11320 | 35.01 | 43.37 |
| 11 | A. niger 13219 | 35.38 | 41.34 |
| 12 | A. niger 62517 | 35.63 | 41.71 |
| 13 | A. aculeatus 2053 | 18.52 | 36.34 |
| 14 | T. reesei | 15.10 | 33.53 |
| 15 | control | 6.25 | 29.18 |

From the hydrolysis results set forth in Table 10, above, it can be seen that *A. niger* strain numbers 322 and 341 gave higher reducing sugar and total sugar concentrations than the other strains. It can also be seen that all of the *A. niger* strains had a higher level of sugar release than either *A. aculeatus* 2053 or *T. reesei*.

Conclusion

Based on the enzyme production results, it can be concluded that seven *A. niger* strains (NRRL numbers 322, 341, 348, 363, 2270, 13201, 13219) have significantly better enzyme productivity than the other strains tested. From the results of hydrolysis, two *A. niger* strains, numbers 322 and 341, gave higher hydrolysis efficiency, as measured by the release more sugars from soy flour. Of the strains tested, it can be concluded that *A. niger* strain numbers 322 and 341 are best suited to the process.

Example 8

Study of Enzymatic Hydrolysis of Soybean Meal Using Fungal Fermentation Broth

Objectives

The enzymatic hydrolysis of soybean meal (SM) using fungal fermentation broth has been studied in this experiment. A systematic study was done to see the effect of four different operating conditions, namely the pH (4-6), the temperature (40-60 C), and the enzyme to substrate ratio (10-2000 U/g of soybean meal), on the enzymatic hydrolysis in order to maximize the reducing sugar and total carbohydrate release.

Enzymatic Hydrolysis

Enzymatic hydrolysis experiments for soybean meal were conducted under different operating conditions using a broth collected from *Aspergillus niger* fermentation. All experiments were carried out in 250 ml Erlenmeyer flasks with a total working volume of 50 ml in an incubator shaker for about 2 days. Operating conditions studied in these experiments were pH, temperature and enzyme/substrate ratio. All of the systems were supplemented with 0.05% sodium azide to prevent the growth of microorganisms. The flasks were agitated in the incubator shaker at 250 rpm to ensure adequate mixing of the substrate. Assays without enzyme were carried out as control. Samples were taken in regular interval and centrifuged at 10000 rpm for 10 minutes and the supernatant was stored for analysis of the reducing sugars and total carbohydrate concentration.

Design of Experiments

One part of the experiment was designed to investigate the effect of pH on the enzymatic hydrolysis efficiency based on the sugar release. Seven systems were studied by adjusting the pH from 3.2 to 6 by adding 5M HCl, while keeping all other conditions same. The temperature, enzyme/substrate ratio and substrate to liquid ratio were maintained 50 C, 50 Units/g of soybean meal and 1:4 (wt:vol), respectively for all the systems. Assays without enzyme were carried out as control.

A second part of the experiment was designed to investigate the effect of temperatures between 40° C. and 60° C. on enzymatic hydrolysis efficiency based on the sugar release. five systems were studied by adjusting the temperature from 40° C. and 60° C., while keeping all other conditions same. The pH, enzyme to substrate ratio and substrate to liquid ratio were maintained 4.8, 50 Units/g of soybean meal and 1:4 (wt:vol), respectively for all the systems. Assays without enzyme were carried out as control.

A third part of the experiment was designed to investigate the effect of enzyme to substrate ratios between 10 Units/g and 474 Units/g of soybean meal on enzymatic hydrolysis efficiency based on the sugar release. Seven systems were studied by adjusting substrate ratios from 10 to 474 Units/g of soybean meal, while keeping all other conditions same. The temperature, pH, and substrate to liquid ratio were maintained 50° C., 4.8, and 1:4 (wt:vol), respectively for all the systems. Assays without enzyme were carried out as control.

Analytical Methods

Reducing sugar concentration was measured according to the standard procedure using the DNS method. 100 ml of diluted sample, 900 ml of DI water and 3 ml of DNS reagent were pipetted into 25 ml DNS tubes. After heating the samples in boiling water for 5 min, the samples were diluted to 25 ml DI water and absorbance was measured at 550 nm. Total carbohydrate concentration was measured according to standard phenol sulfuric method. 100 ml of diluted sample, 900 ml of DI water, 1 ml of phenol reagent and 5 ml of concentrated sulfuric acid were added in test tubes. After 10 min, the reaction mixtures were well mixed and the absorbance was measured at 490 nm.

Results and Discussion

Figure 22:
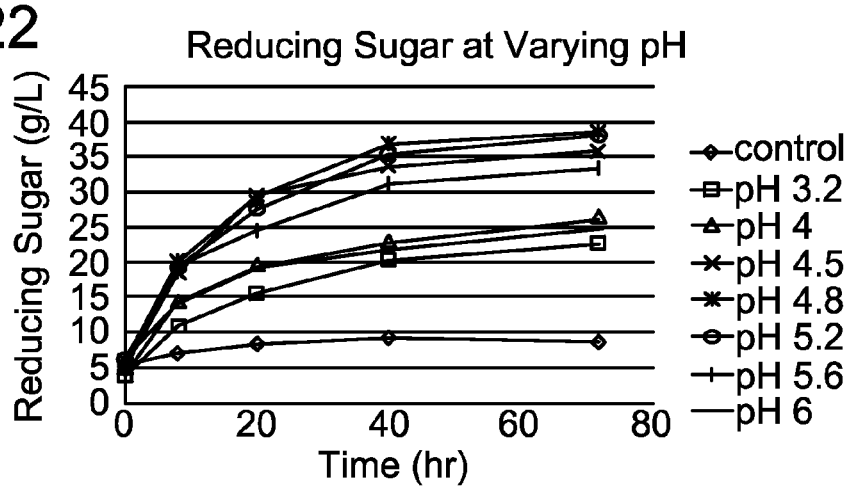
FIG. 22 is a graph showing time profiles of reducing sugar concentrations released from the hydrolysis of soybean meal conducted at different pH values using an *A. niger* enzyme broth prepared according to at least one embodiment of the present invention.
Figure 23:
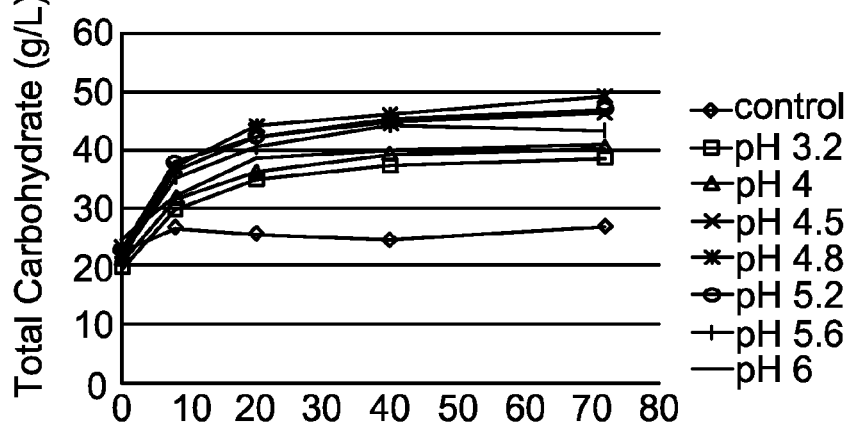
FIG. 23 is a graph showing time profiles of total carbohydrate concentrations released from the hydrolysis of soybean meal conducted at different pH values using an *A. niger* enzyme broth prepared according to at least one embodiment of the present invention.

FIG. 22 and FIG. 23 show the reducing sugar and total carbohydrates concentration, respectively for the different pH systems at a fixed enzyme to substrate ratio and temperature. As can be seen in FIGS. 22 and 23, the pH has greater effect on the reducing sugar concentrations than it does on the total carbohydrate concentration, implying that pH has stronger effect on the degradation of the oligomers to monomers, than on the degradation of polymers to oligomers. A change in pH of from 4.5 to 5.6 did not have significant effect on reducing sugar but a pH lower than 4 and higher than 5.6 gave much lower reducing sugar. Within this range, pH 4.8 and 5.2 gave highest reducing sugar concentration. A pH 4.8 of also gave highest total carbohydrate concentration. So, it can be concluded that pH 4.8 to 5.2 would be optimum pH for maximizing the reducing sugar and total carbohydrate concentration.

Figure 24:
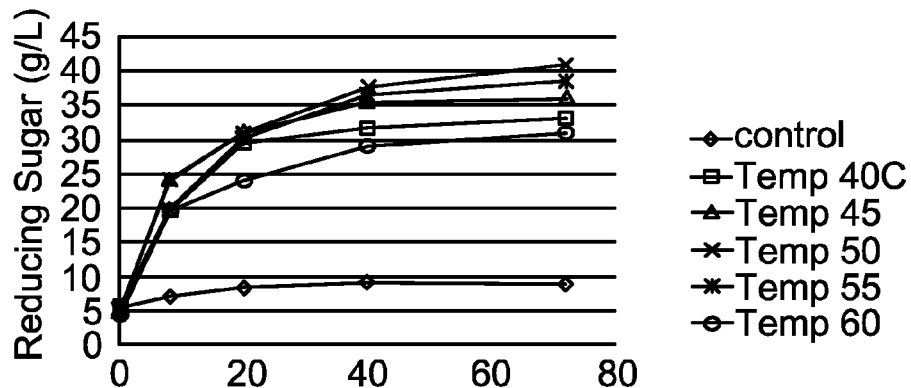
FIG. 24 is a graph showing time profiles of reducing sugar concentrations released from the hydrolysis of soybean meal conducted at different temperatures using an *A. niger* enzyme broth prepared according to at least one embodiment of the present invention.
Figure 25:
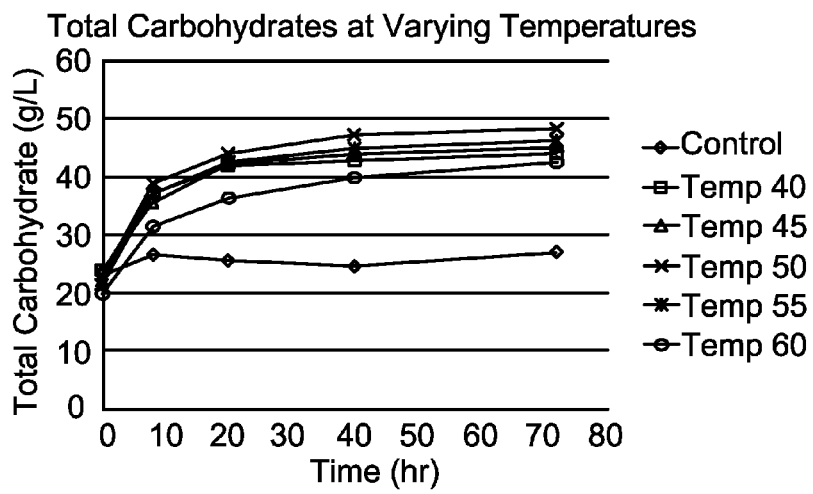
FIG. 25 is a graph showing time profiles of total carbohydrate concentrations released from the hydrolysis of soybean meal conducted at different temperatures using an *A. niger* enzyme broth prepared according to at least one embodiment of the present invention.

FIGS. 24 and 25 show the reducing sugar and total carbohydrates concentrations, respectively for the different temperature systems at a fixed pH and enzyme to substrate ratio. It was found that an increase in temperature from 40° C. to 50° C. at a fixed enzyme to substrate ratio and pH leads to a increase in reducing sugar and total carbohydrate concentration whereas an increase in temperature from 50° C. to 60° C. had the opposite effect on the in reducing sugar and total carbohydrate concentration. It was concluded that 50° C. was optimal for releasing highest amount of reducing sugar and carbohydrates.

Figure 26:
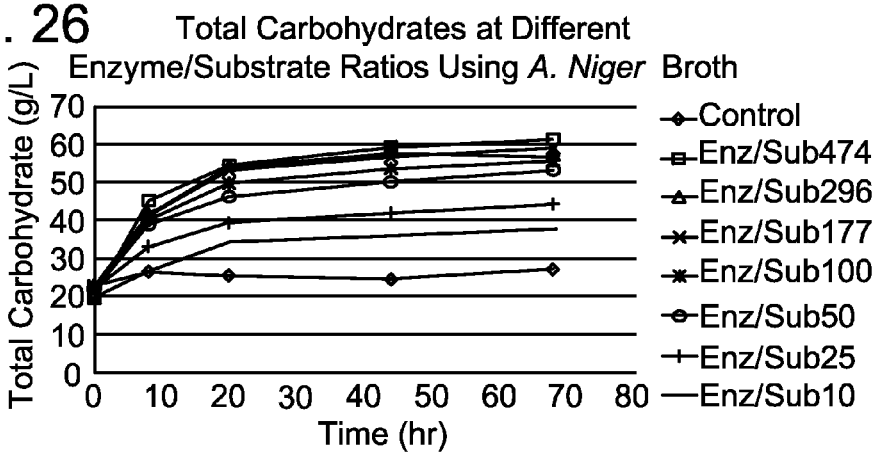
FIG. 26 is a graph showing time profiles of total carbohydrate concentrations released from the hydrolysis of soybean meal conducted with different enzyme-to-substrate ratios, in terms of summed activity units of cellulase, xylanase and pectinase per g of dry soybean meal, using an *A. niger* enzyme broth prepared according to at least one embodiment of the present invention.
Figure 27:
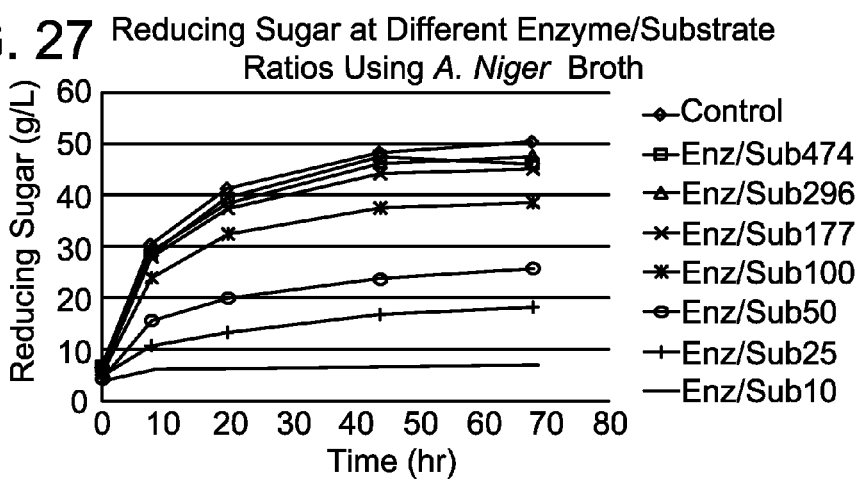
FIG. 27 is a graph showing time profiles of reducing sugar concentrations released from the hydrolysis of soybean meal conducted with different enzyme-to-substrate ratios, in terms of summed activity units of cellulase, xylanase and pectinase per g of dry soybean meal, using an *A. niger* enzyme broth prepared according to at least one embodiment of the present invention.

For the systems wherein the enzyme to substrate ratio was varied at a fixed pH (4.8) and temperature (50° C.) both reducing sugar and total carbohydrate concentrations in hydrolysates increased with an increase in the enzyme to substrate ratio. As can be seen in FIG. 26 and FIG. 27, the production of reducing sugars increased from 18 g/l at an enzyme to sub ratio of 10 Units/g to about 50 g/l at an enzyme to sub ratio of 474 Units/g. Likewise, the total carbohydrate concentration increased was from 35 g/l at an enzyme to sub ratio of 10 Units/g to about 60 g/l at an enzyme to sub ratio of 474 Units/g. As can be seen in FIGS. 26 and 27, there is a dramatic increase in both reducing sugar and total carbohydrate concentrations as the enzyme to substrate ratio was increased from 10 Units/g to about 100 Units/g, but there was only a slight improvement in the reducing sugar and total carbohydrate concentrations as the enzyme to sub ratio was increased from 100 Units/g to about 474 Units/g. It was concluded that this small improvement did not justify the increased expense if increasing the enzyme to substrate ratio beyond 100 Units/g.

Conclusion

From the analysis of results it can be concluded that enzyme to substrate ratio of 100 Units/g, a pH of 4.8-5.2 and temperature of 50° C. are the optimum operating conditions for maximizing the hydrolysis yield using the enzyme broth.

Example 9

Recovery or Soluble Protein by Ethanol Precipitation

This experiment was designed to determining the optimum ratio of ethanol to hydrolysate for generating the maximum amount soy protein isolate. Hydrolysate was collected after separating the soy protein concentrate from the hydrolysis mixture by centrifugation. This is an alternate method of collecting soy protein isolate by heat treatment. 10 ml of hydrolysate was taken and ethanol was added in a of volumetric ratio of ethanol to hydrolysate of from about 0.2 to about 2. The soluble protein in the hydrolysate precipitated out of solution after being denatured by the ethanol. The precipitated soy protein isolate was collected by centrifugation and its dry weight was measured and recorded. The experiment was done at room temperature.

Figure 28:
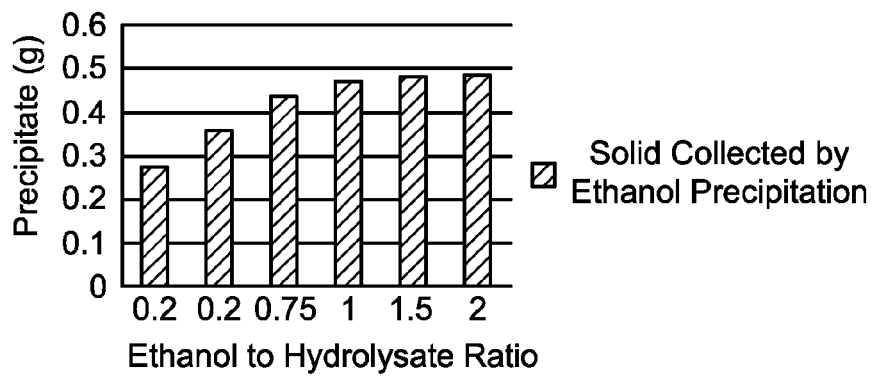
FIG. 28 is a graph showing the dry weight of protein recovered from hydrolysate by the method of ethanol precipitation with at different ethanol to hydrolysate volume ratios.

The results of the experiment are shown in FIG. 28. As can be seen in FIG. 28 the dry weight of precipitant increases as the ethanol to hydrolysate ratio is increased from 0.2 to about 1.0. It is evident from FIG. 28 that an ethanol to hydrolysate ratio of more than 1 did not increase the SPI recovery. So it can be concluded that SPI recovery can be maximized (about 0.48 g per 10 ml) using ethanol to hydrolysate ratio of 1. Accordingly, it was concluded that an ethanol to hydrolysate ratio of 1 is the optimized ratio for recovering maximum amount of soy protein isolate.

Example 10

MIC Study of Benzoic Acid for the Growth of *Debaryomyces hansenii*

Experimental Design

Sodium benzoate (Na.B) was used to inhibit the bacterial growth present as spores in the soy flour that was being used for enzyme hydrolysis enrichment of the soy proteins. Different sodium benzoate concentrations were studied to determine the best concentration of sodium benzoate to inhibit bacterial growth. It was determined that Na.B level of 2 g/L was effective. The hydrolysate byproduct of enzyme hydrolysis of the soy flour having different sugars was intended to be used for arabitol production using *Debaryomyces hansenii*. In order for this enzyme hydrolysate to be suitable for arabitol production, however, the sodium benzoate must be removed. Accordingly, the maximum concentration that could remain in the hydrolysate that is not inhibitory for *D. hansenii* growth was determined by this MIC of Na.B test with *D. hansenii*.

The removal of Na.B by GAC adsorption was described in another report but in the removal process (see Example 13), the Na.B was converted to benzoic acid by the addition of HCl. Accordingly, these MIC studies were done using benzoic acid on *D. hansenii* instead of sodium benzoate. Benzoic acid concentrations that were considered were from 0.01 to 0.25 g/L and were compared with no benzoic acid concentration.

Materials and Methods

*D. hansenii* was inoculated first in a pre-culture medium with the following medium composition (g/L): Glucose 10, Peptone 5, Malt extract 3 and yeast extract 3. A pre-culture was performed in a 250 ml Erlenmeyer flask with 50 ml culture volume in an orbital shaker at 250 rpm and at a temperature of 30° C. After 36 hours, 5% inoculum is transferred into systems with the different benzoic acid concentrations shown in Table 11 and the medium composition shown in Table 12, each system in a 250 ml Erlenmeyer flask with a 50 ml working volume. These flasks were placed in an orbital shaker at 250 rpm and a temperature of 30° C. Samples were taken every 24 h for 3 days and the pH and cell concentrations were measured and recorded.

TABLE 11

Benzoic acid concentrations used for MIC studies with *D. hansenii*.

| Systems | Benzoic acid (g/L) |
|---|---|
| 1 | 0.25 |
| 2 | 0.10 |
| 3 | 0.05 |
| 4 | 0.025 |
| 5 | 0.01 |
| 6 | 0.00 |

TABLE 12

Medium composition used for MIC of benzoic acid for *D. hansenii* growth.

| Medium | g/L |
|---|---|
| Yeast Extract | 6 |
| (NH4)2SO4 | 4 |
| K2HPO4 | 0.32 |
| KH2PO4 | 0.21 |
| MgSO4•7H2O | 1 |
| Glucose | 80 |

Cell Growth

Cell growth was measured as optical density (OD) by measuring the absorbance of the washed cells at 610 nm with UV-vis spectrophotometer. A known amount of sample was centrifuged at 8000 rpm for 10 min and the supernatant was separated and saved for further analysis. Cell pellet was washed with DI water and centrifuge again under same conditions. Cell pellet was dispersed in water and the absorbance was measured at 610 nm.

Results

Figure 29:
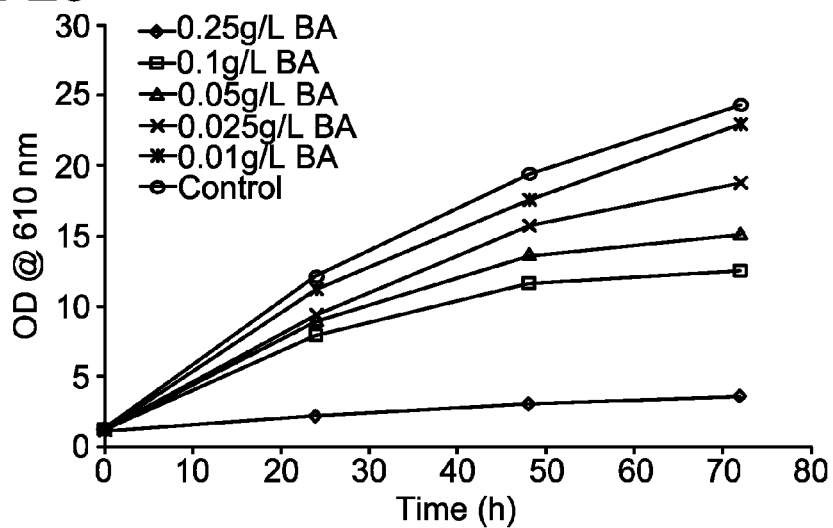
FIG. 29 is a graph showing cell growth of *Debaryomyces hansenii*, measured as optical density at 610 nm ($OD_{610}$), in media with different benzoic acid concentrations prepared according to at least one embodiment of the present invention.

Benzoic acid concentrations of 0.01, 0.025, 0.05, 0.1 and 0.25 g/L were tested for *D. hansenii* growth in comparison to that of no benzoic acid. Cell growth for these systems was measured as OD and the cell growth profile for each of these systems is shown in FIG. 29. As can be seen in Table 13 and FIG. 29, the system with 0.25 g/L benzoic acid showed almost no cell growth and rest of the systems (all having benzoic acid concentrations of 0.01 g/L or more) had slow growth as shown in Table 13, below. The System having a benzoic acid concentration of 0.01 g/L, however, showed very little inhibitory effect on *D. hansenii* growth and was comparable with that of the control.

TABLE 13

Specific growth rate of *D. hansenii* in systems with different benzoic acid concentration.

| Benzoic acid (g/L) | Specific growth rate(μ), (h$^{-1}$) |
|---|---|
| 0.25 | 0.022 |
| 0.10 | 0.075 |
| 0.05 | 0.079 |
| 0.025 | 0.082 |
| 0.01 | 0.089 |
| 0.00 | 0.092 |

Figure 30:
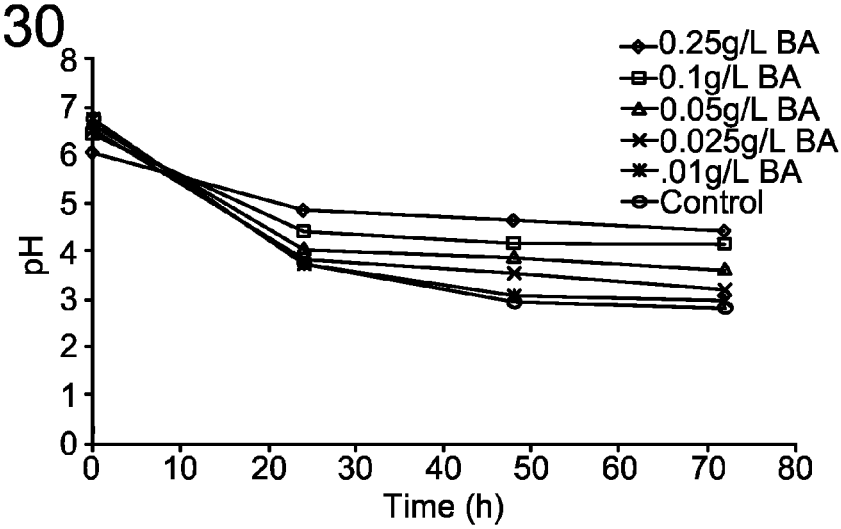
FIG. 30 is a graph showing the profiles of pH change for *D. hansenii* cultures grown in media with different benzoic acid concentrations prepared according to at least one embodiment of the present invention.
Figure 31:
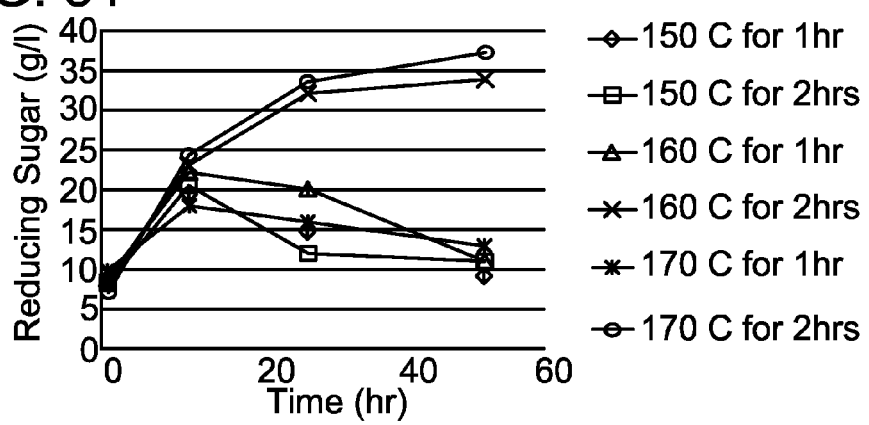
FIG. 31 is a graph showing reducing sugar profiles from hydrolysis of the soybean meal samples that had been dry-heat-sterilized at different temperatures and/or for different durations prepared according to at least one embodiment of the present invention. The profiles showing decrease in later stages indicated microbial consumption of reducing sugars and, accordingly, incomplete sterilization at those treatment conditions.

FIG. 30 shows the pH profile for these systems over the span of 3 days. The initial pH in all the systems was around 6.7 and decreased gradually over time.

Discussion

MIC of benzoic acid against the growth of *D. hansenii* is 0.0.25 g/L. When sodium benzoate was used for the enzyme hydrolysis of soy flour, it has to be separated from the hydrolysate left after the enzyme hydrolysis, since *D. hansenii* growth is reduced by the presence of benzoic acid concentration higher than 0.01 g/L. Though the cell growth is not completely inhibited at benzoic concentrations up to 0.1 g/L, it is reduced. This increases the lag phase of the cells, thereby increasing the run time for arabitol production. For another strain of *Debaryomyces hansenii*, the MIC concentration of benzoic acid has been found to be around 0.4-0.5 g/L. (See J. S. P Michael Davidson, A L Branen. (2005) Antimicrobials in food, Third ed., CRC press, the disclosure of which is incorporated herein by reference in its entirety).

Example 11

Evaluation of Temperatures for Heat Sterilization of Soybean Meal

The temperatures required for dry heat sterilization of soybean meal were evaluated to identify a method of reducing the growth of bacteria, thereby improving the total sugar yield from hydrolysis by eliminating the sugar consumption from bacterial growth.

Experimental Design

Soybean meal enzyme hydrolysis was done at 50° C. and pH 4.8. Usually in enzyme hydrolysis process, sodium azide was used to avoid any growth of bacteria during the hydrolysis. Sodium azide is a strong inhibitor for bacteria and other microorganisms such as yeast species. The present process contemplates that the enzyme hydrolysate be used for arabitol production. It is therefore critical to develop a method of reducing the growth of bacteria while not rendering the hydrolysate unsuitable for arabitol production.

Procedure and Materials & Methods

Heat sterilization of defatted soybean meal was done in an oven and was studied for 3 temperatures, 150, 160 and 170° C., with each temperature being tested at intervals of 1 and 2 hours. These 6 different studies are shown in Table 14, below.

TABLE 14

Heat sterilization systems considered.

| System | Temperature (° C.) | Duration (hours) |
|---|---|---|
| 1 | 150 | 1 |
| 2 | 150 | 2 |
| 3 | 160 | 1 |
| 4 | 160 | 2 |
| 5 | 170 | 1 |
| 6 | 170 | 2 |

Defatted soybean meal having a dry weight of 10 g was heated in an oven at the temperatures and times set forth in Table 14 and then mixed with enzyme broth (about 8 ml) having the enzyme activities shown in Table 15, below and water to make the final volume to 50 ml thereby making the system to 200 g/L soybean meal.

TABLE 15

Measured enzyme activity of cellulase, xylanase and pectinase for heat sterilization studies

| Enzyme | Activity, (U/ml) |
| --- | --- |
| Cellulase | 0.35 |
| Xylanase | 60.6 |
| Pectinase | 2.1 |
| Total | 63.1 |

These studies were done in 250 ml Erlenmeyer flasks, and the enzyme hydrolysis was performed in the orbital shaker at 250 rpm and a temperature of 50° C. The pH of the systems was adjusted to be about 4.8, before the flasks were agitated in the shaker. Samples were collected at 12, 28 and 52 hours of hydrolysis and the concentration of released sugars measured.

Total Sugar Measurement

Concentration of all the sugars present in the sample was measured using phenol sulfuric acid test as follows. First, 1 ml of sample was mixed with 1 ml of a 5% phenol solution in a glass test tube. Then, 5 ml of concentrated sulfuric acid (98%) was added to these and allowed to cool to room temperature for 5 min. The absorbance of the samples was measured at 490 nm. A calibration curve was developed using glucose as the standard and following the same procedure.

Reducing Sugar Measurement

The reducing sugar concentration was measured follows. First, 1 ml of sample was mixed with 3 ml of DNS reagent in glass test tube. These tubes were placed in boiling water for 5 min. Samples were then allowed to cool down to room temperature and DI water was added to the tubes to 25 ml. Samples were then mixed and absorbance was measured at 550 nm. Glucose was used as the standard for the calibration following the same procedure.

Results and Discussion

Figure 32:
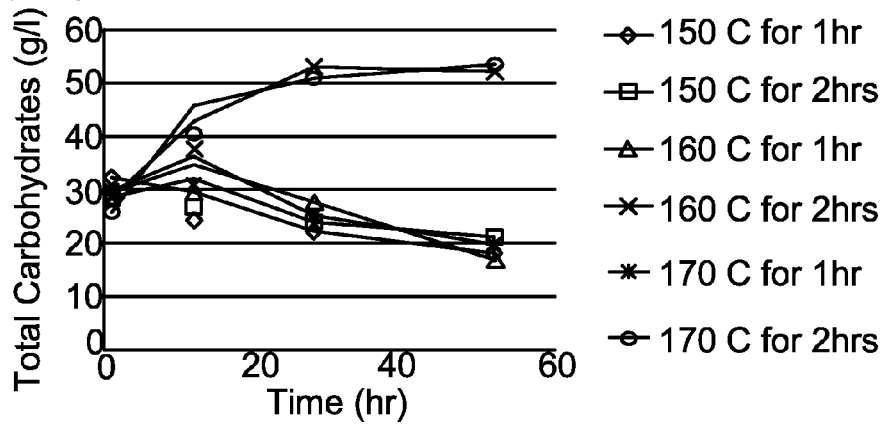
FIG. 32 is a graph showing total carbohydrate profiles from hydrolysis of the soybean meal samples that had been dry-heat-sterilized at different temperatures and/or for different durations prepared according to at least one embodiment of the present invention. The profiles showing decrease in later stages indicated microbial carbohydrate consumption and, accordingly, incomplete sterilization at those treatment conditions.

Reducing and total sugar concentrations in each system were measured and recorded at different times during enzyme hydrolysis. The reducing sugar profiles are shown in FIG. 30 the total sugar profiles are shown in FIG. 32. In both the reducing and total sugar profiles, it can be seen that System 4 and System 6, which were the systems having soybean meal heat treated at 160° C. (System 4) and 170° C. (System 6) for 2 hours, showed continuous increase in the sugar concentration with time. All of the other systems, showed a clear release of both reducing and total sugars through the first 12 hours, before the sugar concentrations began to decrease, suggesting that the sugars were being consumed by bacteria for their growth.

Figure 33:
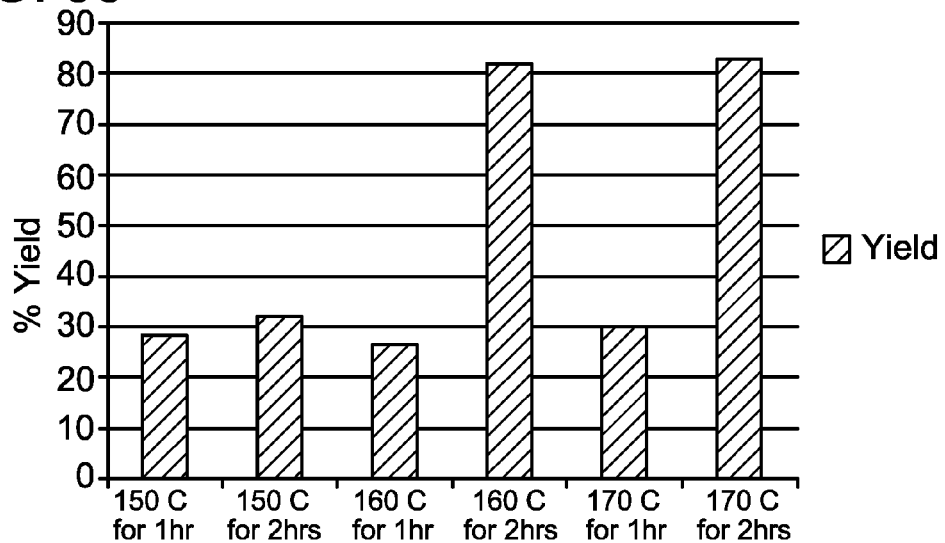
FIG. 33 is a graph showing yields of total carbohydrate from hydrolysis of the soybean meal samples that had been dry-heat-sterilized at different temperatures and/or for different durations, prepared according to at least one embodiment of the present invention. The systems giving lower yields were due to microbial carbohydrate consumption, corresponding to incomplete sterilization at those treatment conditions.

These profiles suggest that either 160° C. of 170° C. is enough for sterilization, but should be done for 2 h. The total sugar released was 52 g/L and reducing sugar was 34-37 g/L for these two systems. As soybean meal has about 32% carbohydrates, the yield of sugar released could be determined and is shown in FIG. 33. Systems 4 and 6 had an 80% yield, which was more than twice that of any of the other Systems.

Example 12

Study of Methods for Sterilization of Soybean Meal

Experimental Design

Preservatives such as sodium benzoate and sodium nitrite were used to evaluate their effectiveness as inhibitors for bacterial growth. Other methods that were evaluated are autoclaving the soybean meal in water and a dry soybean meal vacuum autoclave at two different time periods. The concentrations of reducing sugars in these systems during the enzyme hydrolysis were compared. These results were compared with that of no sterilization step.

Procedure and Materials & Methods

Systems that were considered in this section are identified on Table 16. All the systems contain 10 g of soybean meal. The enzyme hydrolysis was performed in 250 ml Erlenmeyer flasks which were agitated in orbital shaker at 250 rpm and at 50° C.

For control system, only water was added (no enzyme was added). For non-sterilized system, 10 g of soybean meal was mixed with 4 ml of enzyme broth and about 70 ml DI water. In the case of liquid autoclave system, 10 g of soybean meal was mixed with about 40 ml DI water and was autoclaved for 15 min. After autoclaving, an additional 30 ml of DI water (sterile) and 4 ml of enzyme broth were added. For vacuum autoclave systems, 10 g of soybean meal was autoclaved dry under vacuum cycle in the autoclave with no water for 15 and 45 min, respectively. After the autoclave cycle, 4 ml of enzyme broth and an additional 30 ml of DI water (sterile) was added. In case the sodium benzoate and sodium nitrite systems, 10 g of soybean meal was mixed with 2 g/L of either sodium benzoate or sodium nitrite, enzyme broth and DI water. There was no autoclaving or heating step used in these preservatives systems. The activity of the enzymes in the broth used for these experiments is shown on Table 17. The pH of all of the systems was adjusted to 4.8. Samples were taken periodically for the measurement of reducing sugars.

TABLE 16

Systems considered for effective sterilization of soybean meal

| System |
| --- |
| Control |
| Non-sterilized |
| Liquid autoclave |
| Vacuum autoclave (dry)-15 min |
| Vacuum autoclave (dry)-45 min |
| Sodium Benzoate (2 g/L) |
| Sodium nitrite (2 g/L) |

TABLE 17

Enzyme activities for hydrolysis.

| Enzyme | Activity (U/ml) |
| --- | --- |
| Cellulase | 2.3 |
| Xylanase | 70.0 |
| Pectinase | 7.8 |
| Total | 80.0 |

Reducing Sugars

The method is same as that described in Example 11, above.

Total Sugar Measurement

The method is same as that described in Example 11, above.

Results and Discussion

Figure 34:
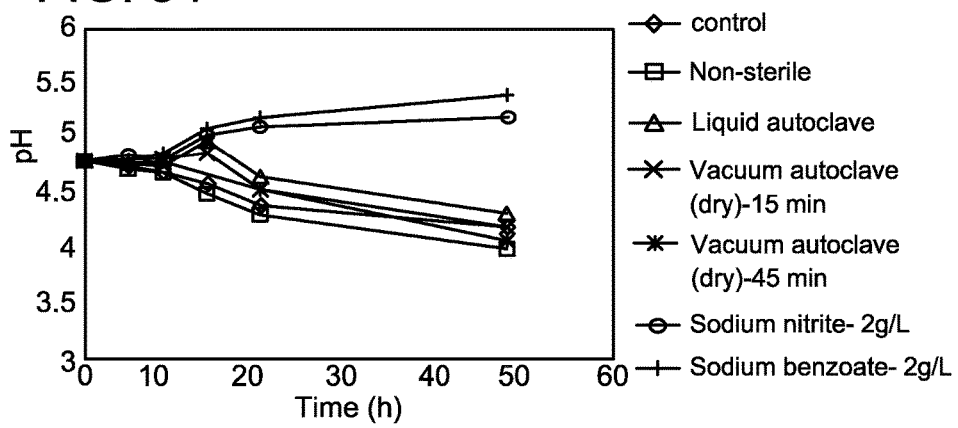
FIG. 34 is a graph showing pH profiles for enzyme-free control and enzyme-containing systems without and with different methods attempted for preventing microbial growth during soybean meal hydrolysis process prepared according to at least one embodiment of the present invention.

FIG. 34 shows the pH profiles for all the treatments to soybean meal tested for reducing the bacterial growth and improving the enzyme hydrolysis. As set forth above, the initial pH in all the systems was adjusted to 4.8 before the enzyme hydrolysis. As seen from the profile, however, the pH in all the systems declined over the time, except for systems with preservatives sodium benzoate and sodium nitrite. The reduction in the pH over the time shows the acid production from bacterial growth due to the consumption of sugar and release of organic acids. In case of systems using the preservatives, it is clear from the pH profile that there was no acid production, and accordingly, shown an absence of bacterial growth.

Figure 35:
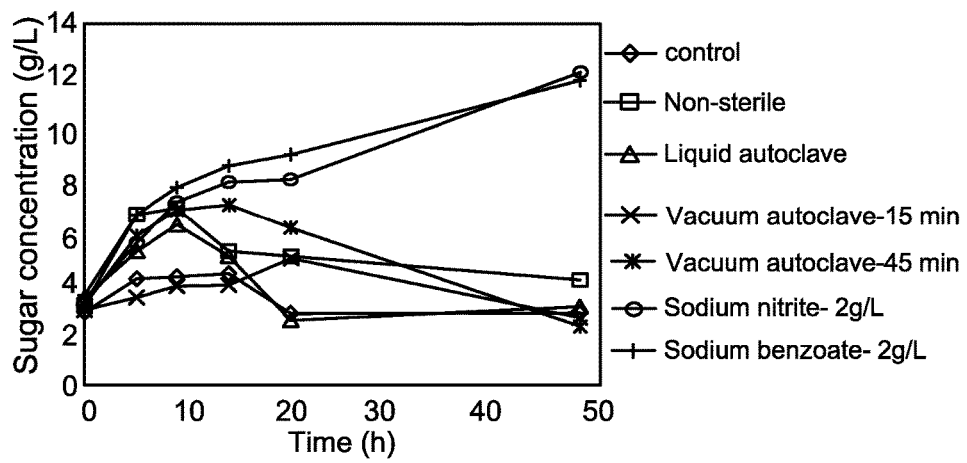
FIG. 35 is a graph showing reducing sugar concentration profiles for enzyme-free control and enzyme-containing systems without and with different methods attempted for preventing microbial growth during soybean meal hydrolysis process prepared according to at least one embodiment of the present invention.

At around 10 h, the released sugar concentration was similar in all the systems (in the range of 7-9 g/L) except for the control and the 15 min vacuum autoclave system. The reducing sugar concentration profiles are shown in FIG. 35. After 10 h, however, the sugar concentration values increase in the systems with the preservatives sodium benzoate and sodium nitrite, but not in the other systems. These systems showed lower and reduced sugar concentrations over the time, indicating the consumption of sugar for bacterial growth.

These results clearly show that among the different treatments that were considered in this study, use of preservatives proved to be the best solution for considering in the soybean meal enzyme hydrolysis for the reduction of any bacterial growth thereby improving the yield of enzyme hydrolysis.

Example 13

Removal of Sodium Benzoate

Sodium benzoate was used in the sterilization of soy for enzyme hydrolysis process for preventing the growth of bacteria. The carbohydrates released in this process were intended to be applied in another fermentation process for the production of valuable products such as arabitol. Sodium benzoate that was used in the enzyme hydrolysis process ends up in the liquid portion with all the carbohydrates after the enzyme hydrolysis step. It is important to remove the sodium benzoate from the liquid broth before it is applied to any fermentation process as it inhibits the growth of any other microorganism too such as yeast or fungus or other bacteria.

In our study, we tried to remove the sodium benzoate by two methods. One method was using extraction method using butanol. Another method was to remove by adsorption method on to granulated activated carbon (GAC). Enzyme hydrolysate was originally intended to go through acid hydrolysis (autoclaving under acidic conditions, to breakdown most of the sucrose into monomers) and this low pH conditions the sodium benzoate will be benzoic acid and our studies are done on the removal of benzoic acid from the hydrolysate.

Different butanol and GAC concentrations were used to find the optimal method of removal of sodium benzoate as benzoic acid. Details of the experiment are described in the next section.

Experimental Design

1. Butanol Adsorption 10 ml of enzyme hydrolysate (which is the supernatant after centrifugation of the enzyme hydrolysate broth at 9000 rpm for separating the solid and liquid portion) was extracted with 10 ml and 20 ml of butanol at 3 different pH as shown in Table 18. These extractions were done in 40 ml vials and placed on disc rotator rotating at 25 rpm for 24 hours. Benzoic acid concentration is measured both in aqueous phase and organic phase by HPLC and the method is described in the following sections.

TABLE 18 pH conditions and butanol volumes considered for the sodium benzoate extraction studies.

| pH | Volume of sample, ml | Volume of butanol, ml |
|---|---|---|
| 2.5 | 10 | 10 |
|  | 10 | 20 |
| 4 | 10 | 10 |
|  | 10 | 20 |
| 4.8 | 10 | 10 |
|  | 10 | 20 |

2. GAC Adsorption

Enzyme hydrolysis obtained after centrifugation of the enzyme hydrolysate broth, was adjusted to pH around 2 by 12.1 N HCl and heat treated (at 100 C for 20 min) for further separation of proteins from the hydrolysate. These solids are separated by centrifugation at 9000 rpm for 10 min, and the liquid was treated with different GAC concentrations for benzoic acid removal.

GAC concentrations of 2-14 g/L were considered meaning for every 1 L of liquid hydrolysate, 2-14 g of GAC was considered. 10 ml of sample was considered in each set of study, and adsorption was carried in 40 ml vials on rotating disc at 25 rpm for 24 hours. After 24 hours, samples were centrifuged and liquid portion was analyzed for benzoic acid concentration using HPLC.

Materials and Methods

1. HPLC Method for Benzoic Acid Separation

Benzoic acid concentrations were measured using Supelco LC-18 column with mobile phase containing 82% of 0.5% (v/v) acetic acid in water and 18% of acetonitrile. Column temperature was maintained at 30° C. and flow rate of the mobile phase was 1 ml/min. Benzoic acid was measured via UV detector at 280 nm.

Benzoic acid (BA) standards with 0.5 to 0.005 g/L concentrations were used to develop the calibration curve to calculate the concentrations of the benzoic acid in the sample from area measurement of BA peaks.

Results and Discussion

1. Butanol Extraction

Figure 36:
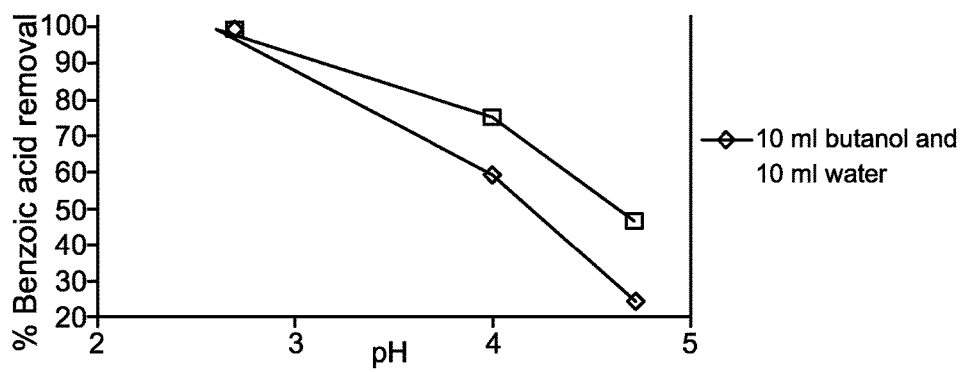
FIG. 36 is a graph showing the percent of benzoic acid removed under different pH and different butanol-to-hydrolysate volume ratios. These percentages were calculated based on the measured benzoic acid concentrations in the hydrolysate before and after the butanol extraction.

Benzoic acid removed after the adsorption process at different pH and butanol contents is shown in FIG. 36. It was clear that when the pH is adjusted to around 2, most of the benzoic acid was extracted in the organic phase in both 10 and 20 ml of butanol. For removal of about 1.4 g/L benzoic acid almost completely or 98% about 10 ml of butanol was needed.

Table 19 shows the volume of aqueous and organic phases after mixing sample and two butanol volumes (10 and 20 ml). Water and butanol are soluble in each other to some extent and their solubility is: water is about 205 g/L in butanol and butanol is 80-85 g/L in water. This shows that there will be some butanol ending up in the hydrolysate broth after removing benzoic acid. This butanol has to be further removed, in order to avoid the growth inhibition for yeast cells (for arabitol production) from butanol.

TABLE 19

Volume of aqueous and organic phase at different butanol contents.

| System | Volume of aqueous phase, ml | Volume of organic phase, ml |
|---|---|---|
| 1 | 7.6 | 12.4 |
| 2 | 4.4 | 25.6 |

2. GAC Adsorption for Benzoic Acid Removal

After subjecting the enzyme hydrolysate to GAC adsorption, benzoic acid concentrations were measured using HPLC and the % benzoic acid that was removed is shown in Table 20. Initial benzoic acid concentration in all the samples was about 1 g/L. With 14 g/L GAC, about 91% of the initial benzoic acid was removed from the hydrolysate. At least 14 g/L GAC was required for adsorption of 92% of the benzoic acid present in the enzyme hydrolysate.

TABLE 20

Percent benzoic acid removed from different GAC concentrations from the enzyme hydrolysate.

| Sample | % Benzoic acid removed |
|---|---|
| 2 g/L GAC | 32 |
| 4 g/L GAC | 53 |
| 6 g/L GAC | 74 |
| 8 g/L GAC | 81 |
| 10 g/L GAC | 88 |
| 12 g/L GAC | 90 |
| 14 g/L GAC | 92 |

What is claimed is:

1. An enzyme based method of separating protein from a protein-containing material derived from soy beans comprising the steps of:
    A. producing a liquid enzyme medium comprising at least one cellulase, at least one hemicellulase, and at least one pectinase by submerged fungal fermentation of a soy hull substrate using a fungus selected from the group consisting of *Aspergillus niger* NRRL 322, *Aspergillus niger* NRRL 341, *Aspergillus niger* NRRL 348, *Aspergillus niger* NRRL 2270, *Aspergillus niger* NRRL 13201, *Aspergillus niger* NRRL 13219, and combinations thereof;
    B. combining said protein-containing material derived from soy beans with said liquid enzyme medium;
    C. agitating the combination of step B, wherein said liquid enzyme medium hydrolyzes the polysaccharides and oligosaccharides contained in said protein-containing material derived from soy beans into saccharides that are soluble in said liquid enzyme medium to provide a mixture comprising a saccharide-containing liquid and a solid protein material; and
    D. separating and collecting the solid protein material from the saccharide containing liquid of the mixture of step C.

2. The method of claim 1 further comprising the step of:
    E. drying the collected solid protein material derived from soy beans of step D to form a protein-containing powder.

3. The method of claim 1 further comprising adding one or more additional batches of said protein-containing material derived from soy beans and/or said liquid enzyme medium as the previous batch of said protein-containing material is being hydrolyzed.

4. The method of claim 1 further comprising heating said protein-containing material derived from soy beans to a temperature of from about 155° C. to about 200° C. for a period of from about 30 minutes to 5 hours before step B to reduce the growth of bacterial and other contaminants during hydrolysis.

5. The method of claim 1 wherein the step of agitating (step C) is performed at a temperature of from about 20° C. to about 60° C.

6. The method of claim 1 wherein the combination of step B is agitated in step C for a period of from about 1 hour to about 96 hours.

7. The method of claim 1 wherein the combination of step B is agitated in step C for a period of from about 4 hours to about 48 hours.

8. The method of claim 1 wherein the step of separating and collecting the solid protein material (step D) is performed by centrifugation.

9. The method of claim 1 further comprising adding an antimicrobial agent selected from the group consisting of sodium benzoate, benzoic acid, sodium azide, ethylenediaminetetraacetic acid (EDTA), and sodium nitrite to the combination of step B, the mixture of step C, or both the combination of step B and the mixture of step C.

10. The method of claim 1 wherein step A further comprises:
    (a) forming a seed culture by placing said fungus, a first carbon source, and a first nitrogen source in a container and agitating for from about 12 to about 96 hours at a temperature of from about 20° C. to about 35° C.;
    (b) transferring the contents of said seed culture to a fermentation vessel that contains a medium with soy hulls, a second nitrogen source and water;
    (c) adjusting the pH of the contents of the fermentation vessel to a pH of from about 3 to about 8;
    (d) growing the fungus in the fermentation vessel, thereby producing an enzyme-containing liquid;
    (e) collecting the enzyme-containing liquid of step (d); and
    (f) diluting the enzyme-containing liquid of step (e) with water or an aqueous solution in a ratio of from about 1:1 to about 50:1 water or solution to enzyme-containing liquid to produce said liquid enzyme medium.

11. The method of claim 1 wherein the ratio of said liquid enzyme medium to said protein-containing material derived from soy beans in B. is from about 3:1 to about 10:1 volume to weight.

12. The method of claim 1 wherein said cellulase comprises an endo-glucanase, an exo-glucanase and/or a β-glucosidase; said hemicellulase comprises one or more enzyme selected from the group consisting of xylanase, mannanase, α-galactosidase, α-arabinosidase, β-xylosidase and acetyl xylan esterase; and said pectinase comprises one or more enzyme selected from the group consisting of feruloyl esterases, pectin depolymerases, pectinesterase, polygalacturonase, galacturan 1,4-α-galacturonidase, exo-poly-α-galacturonosidase, pectate lyase, pectate disaccharide-lyase, oligogalacturonide lyase and pectin lyase.

13. The method of claim 1 further comprising:
F. collecting the saccharide-containing liquid of step D, said saccharide-containing liquid further comprising dissolved proteins;
G. precipitating out the dissolved proteins; and
H. collecting the remaining saccharide-containing liquid.

14. The method of claim 13 wherein one or more of the dissolved proteins of step G are precipitated out of the saccharide-containing liquid by heating said saccharide-containing liquid to a temperature of from about 60° C. to about 100° C.

15. The method of claim 13 wherein the dissolved proteins of step G are precipitated out of the saccharide-containing liquid: by adjusting the pH of said saccharide-containing liquid to the isoelectric point of each one of said dissolved proteins; by diluting said saccharide-containing liquid with water or an aqueous solution; or by the addition of ethanol.

16. The method of claim 15 wherein the step of adjusting the pH of the saccharide-containing liquid to the isoelectric point of each one of said dissolved proteins comprises adjusting the pH of the saccharide-containing liquid to a pH of from a pH of about 4.3 to a pH of about 4.7.

17. The method of claim 13 further comprising:
I. collecting the precipitated proteins of step G as a protein isolate.

18. The method of claim 1 wherein said protein-containing material derived from soy beans comprises soybean meal, soy flour, soy flake, and soy powder, and combinations thereof.

19. The method of claim 10 wherein the seed culture of step (a) further comprises an inducer, said inducer inducing said fungus to produce enzymes.

20. The method of claim 10 wherein step (d) further comprising agitating the contents of the fermentation vessel in step (b) and adding air, oxygen, or a combination thereof to the fermentation vessel in step (b) until the enzyme production has substantially stopped.

21. The method of claim 10 wherein said first carbon source is selected from the group consisting of soy beans, soy hulls, potato dextrose, sucrose, lactose, glucose, fructose, maltose, glycerol, the saccharide-containing liquid of step H of claim 13, soluble soy carbohydrates, proteins, lipids, fat, fatty acids, glycerides, and combinations thereof.

22. The method of claim 10 wherein said first nitrogen source is selected from the group consisting of organic nitrogen-containing materials, inorganic nitrogen-containing materials, ammoniums, nitrates, and combinations thereof.

23. The method of claim 10 wherein said first nitrogen source and/or said second nitrogen source is selected from the group consisting of soybean meal, soy flour, corn steep liquor, dairy waste containing milk protein, and a mixture of from about 0 g/L to about 2.65 g/L of ammonium sulfate, from about 0 g/L to about 0.3 g/L of urea, and from about 0 g/L to about 3.47 g/L of proteose peptone.

* * * * *